United States Patent
Demmer et al.

(10) Patent No.: US 10,617,875 B2
(45) Date of Patent: Apr. 14, 2020

(54) FACILITATING URGENCY MODULATED BEACONING RATES FOR MEDICAL DEVICES

(71) Applicant: Medtronic, Inc., Minneapolis, MN (US)

(72) Inventors: Wade M. Demmer, Coon Rapids, MN (US); Charles R. Gordon, Phoenix, AZ (US); Matthew R. Yoder, Crystal, MN (US); Val D. Eisele, New Brighton, MN (US); Matthew P. Hanly, Scottsdale, AZ (US); James R. Peichel, Minneapolis, MN (US); Nicholas C. Wine, Minneapolis, MN (US); Ryan D. Wyszynski, Oak Grove, MN (US); Eric R. Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 65 days.

(21) Appl. No.: 15/472,371

(22) Filed: Mar. 29, 2017

(65) Prior Publication Data
US 2018/0243568 A1 Aug. 30, 2018

Related U.S. Application Data

(60) Provisional application No. 62/464,841, filed on Feb. 28, 2017.

(51) Int. Cl.
*A61N 1/372* (2006.01)
*H04L 12/26* (2006.01)
(Continued)

(52) U.S. Cl.
CPC .......... *A61N 1/3727* (2013.01); *A61B 5/0002* (2013.01); *A61N 1/37258* (2013.01);
(Continued)

(58) Field of Classification Search
CPC ...... H04Q 9/00; H04Q 2209/40; G06F 19/00; G06F 19/3418
(Continued)

(56) References Cited

U.S. PATENT DOCUMENTS

| 5,095,308 A | 3/1992 | Hewitt |
| 7,055,111 B2 | 5/2006 | Scheessele |

(Continued)

FOREIGN PATENT DOCUMENTS

| EP | 2113188 A1 | 11/2009 |
| WO | 2016092241 A1 | 6/2016 |

OTHER PUBLICATIONS

C00012098.WOU3 (PCT/US2018/019312) PCT Notification of Transmittal of the International Search Report and the Written Opinion of the International Searching Authority, dated Jun. 11, 2018, 10 pages.

(Continued)

*Primary Examiner* — Joseph H Feild
*Assistant Examiner* — Sharmin Akhter

(57) ABSTRACT

Techniques for facilitating telemetry between a medical device and an external device are provided. In one example, a medical device includes a classification component and a communication component. The classification component is configured to determine a classification for data generated by the medical device. The classification component is also configured to determine an urgency level for an advertising data packet based on the classification for the data. The communication component is also configured to broadcast the advertising data packet for the medical device at a defined beaconing rate based on the urgency level for the advertising data packet.

28 Claims, 11 Drawing Sheets

(51) Int. Cl.
*A61B 5/00* (2006.01)
*H04L 29/08* (2006.01)
*H04W 4/80* (2018.01)

(52) U.S. Cl.
CPC ........ *A61N 1/37276* (2013.01); *H04L 43/103* (2013.01); *H04L 43/16* (2013.01); *H04L 67/12* (2013.01); *H04W 4/80* (2018.02)

(58) Field of Classification Search
USPC .................................................. 340/870.07
See application file for complete search history.

(56) References Cited

U.S. PATENT DOCUMENTS

| | | | |
|---|---|---|---|
| 7,110,823 B2 | 9/2006 | Whitehurst et al. | |
| 7,653,017 B2 | 1/2010 | Huylebroeck | |
| 7,656,853 B2 | 2/2010 | Albulet | |
| 7,987,378 B2 | 7/2011 | Lee et al. | |
| 8,145,320 B2 | 3/2012 | Corndorf et al. | |
| 8,290,791 B2 | 10/2012 | Patel et al. | |
| 8,412,964 B2 | 4/2013 | Lee et al. | |
| 8,587,427 B2 | 11/2013 | LaLonde et al. | |
| 8,594,801 B2 | 11/2013 | Corndorf et al. | |
| 8,934,425 B2 | 1/2015 | Abedi et al. | |
| 8,959,368 B2 | 2/2015 | Lee et al. | |
| 8,971,807 B2 | 3/2015 | Hillyard | |
| 9,687,658 B2 | 6/2017 | Wu et al. | |
| 9,855,433 B2 | 1/2018 | Shahandeh et al. | |
| 9,894,691 B1 | 2/2018 | Hellman | |
| 2006/0128308 A1 | 6/2006 | Michael et al. | |
| 2009/0058635 A1* | 3/2009 | LaLonde ............ A61N 1/37282 340/539.11 |
| 2009/0063187 A1 | 3/2009 | Johnson et al. | |
| 2011/0160549 A1* | 6/2011 | Saroka ...................... A61B 5/00 600/301 |
| 2011/0202113 A1 | 8/2011 | Persson et al. | |
| 2012/0108922 A1 | 5/2012 | Schell et al. | |
| 2012/0172690 A1 | 7/2012 | Anderson et al. | |
| 2012/0172941 A1 | 7/2012 | Rys | |
| 2012/0220351 A1 | 8/2012 | Kerai et al. | |
| 2013/0076523 A1* | 3/2013 | Kwan ................... A61B 5/0022 340/686.6 |
| 2014/0214104 A1 | 7/2014 | Greenhut et al. | |
| 2014/0330327 A1 | 11/2014 | Thompson-Nauman et al. |
| 2015/0065047 A1 | 3/2015 | Wu et al. | |
| 2015/0133951 A1 | 5/2015 | Seifert et al. | |
| 2015/0148868 A1 | 5/2015 | Shahandeh et al. | |
| 2015/0341785 A1 | 11/2015 | Young et al. | |
| 2018/0021589 A1 | 1/2018 | Wu et al. | |

OTHER PUBLICATIONS

Kivi et al., "Mitigating Implantable Device Power Drain Associated With Stalled Telemetry Sessions", U.S. Appl. No. 15/471,308, filed Mar. 28, 2017, 78 pages.

Schilling et al., "Managing Telemetry Communication Modes of an Implantable Device", U.S. Appl. No. 15/141,421, filed Apr. 28, 2016, 96 pages.

* cited by examiner

FACILITATING URGENCY MODULATED BEACONING RATES FOR MEDICAL DEVICES

RELATED APPLICATIONS

This application claims the benefit of the filing date of a U.S. Provisional Application Ser. No. 62/464,841, filed Feb. 28, 2017, which is incorporated herein in its entirety.

TECHNICAL FIELD

This disclosure relates generally to medical devices and, more particularly, to systems, apparatus, methods and computer-readable storage media that facilitate urgency modulated beaconing rates for medical devices.

BACKGROUND

Modern healthcare facilitates the ability for patients to lead healthy and full lives. Medical devices are often utilized for such medical advances. For example, medical devices such as pacemakers, implantable cardioverter-defibrillators, neurostimulators, and drug pumps can facilitate management with a wide range of ailments, including, but not limited to, cardiac arrhythmias, diabetes, and Parkinson's disease. Patients and medical care providers can monitor the medical devices and assess a patient's current and historical physiological state to identify and/or predict impending events or conditions.

Medical devices are increasing in complexity while shrinking in size. One hurdle to achieving such small and highly functional devices is efficient power management of these medical devices. In particular, many medical devices operate from power sources that have a limited lifespan and/or are not readily replaceable. Numerous processes associated with a medical device directly impact life of a power source of the medical device. For example, a telemetry process between a medical device and another device is generally inefficient and can unnecessarily drain power from a power source of the medical device if not properly managed. Thus, extending life of a power source of a medical device by improving a telemetry process between the medical device and another device and/or by employing modulated beaconing rates for the medical device is highly desirable.

SUMMARY

The following presents a simplified summary of one or more of the embodiments in order to provide a basic understanding of one or more of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include systems, methods, apparatuses and computer-readable storage media facilitating urgency modulated beaconing rates between a medical device and an external device. Although the term "medical device" is used herein, it is understood that in different embodiments, the medical device can be an IMD. In some embodiments, the medical device is or includes an IMD. As such, "medical device" and "IMD" can be used interchangeably herein and all such variations on embodiments are envisaged. In other embodiments, the medical device is or includes a device configured to interact with an IMD. In these embodiments, the medical device can be implanted within a patient or can be employed externally from or on a body of a patient. Additionally or alternatively, both the medical device and/or the IMD can be implanted within a patient.

In one embodiment, a medical device configured to be employed by a patient is provided. The medical device can include: a housing; a memory, within the housing, that stores executable components; circuitry, within the housing, and configured to at least one of obtain sensed physiological data associated with the patient or deliver a therapy to the patient; and a processor, within the housing, that executes the executable components stored in the memory. The executable components can include a classification component and a communication component. The classification component can be configured to determine a classification for data generated by the medical device. The classification component can also be configured to determine an urgency level for an advertising data packet based on the classification for the data. The communication component can be configured to broadcast the advertising data packet for the medical device at a defined beaconing rate based on the urgency level for the advertising data packet. As used herein, a "beaconing rate" can be a speed or a rate (e.g., frequency of occurrence) for broadcasting an advertising data packet during an interval of time. As also used herein, an "advertising data packet" can be a data packet employed for advertising information to other devices and/or for facilitating a connection with other devices. Furthermore, as used herein, a "fixed polling interval" can be a start time and a stop time for repeatedly broadcasting the advertising data packet at the beaconing rate.

In various different embodiments, the communication component can be configured to broadcast the advertising data packet via modulation of the broadcast at the defined beaconing rate. In certain embodiments, the communication component can be configured to increase the defined beaconing rate based on a determination that the urgency level for the advertising data packet corresponds to a defined event associated with the data. In some embodiments, the communication component can be configured to decrease the defined beaconing rate based on a determination that the urgency level for the advertising data packet corresponds to a defined event associated with the data. In one embodiment, the urgency level for the advertising data packet can correspond to a defined event. In another embodiment, the urgency level for the advertising data packet can correspond to a defined medical event associated with the data or a processing event associated with the medical device. In yet another embodiment, the urgency level for the advertising data packet can correspond to a defined medical event associated with a cardiac rhythm reading for the sensed physiological data. In some embodiments, the communication component can be configured to decrease the defined beaconing rate based on a determination that a communication connection is established between the medical device and an external device. In other embodiments, the communication component can be configured to modify the defined beaconing rate based on historical data indicative of a history of data exchanges with respect to an external device. In some embodiments, the communication component can be configured to modify the defined beaconing rate based on time data indicative of a timestamp associated with the broadcast of the advertising data packet. In other embodiments, the communication component can be configured to modify the defined beaconing rate based on a clock associated with a processor (e.g., a time of data). In some embodiments, the defined beaconing rate can be a first defined beaconing rate, and the communication component can be further configured to modify the defined beaconing rate to a second defined beaconing rate based on receipt of input by the medical device. In some embodiments, the defined beaconing rate can be a first defined beaconing rate, and the communication component can be further configured to modify the defined beaconing rate to a second defined beaconing rate based on longevity data indicative of a lifespan period for a battery of the medical device. In some embodiments, the communication component can be configured to broadcast the advertising data packet at the defined beaconing rate via a communication channel associated with a communication protocol utilizing a level of energy consumption that is less than a defined threshold. In one embodiment, the medical device can be an implantable medical device configured to be at least partially implanted within the patient.

In another embodiment, a method is provided. The method can include classifying, by a medical device comprising a processor, data for an advertising data packet associated with the medical device. The method can also include determining, by the medical device, an urgency level for the advertising data packet based on the classifying for the data. Furthermore, the method can include modulating, by the medical device, a beaconing rate for the advertising data packet based on the urgency level for the advertising data packet.

In some embodiments, the modulating the beaconing rate for the advertising data packet can include broadcasting the advertising data packet based on the beaconing rate associated with the urgency level for the advertising data packet. In some embodiments, the modulating the beaconing rate for the advertising data packet can include increasing the beaconing rate based on a determination that the urgency level for the advertising data packet corresponds to a defined event associated with the data. In some embodiments, the modulating the beaconing rate for the advertising data packet can include decreasing the beaconing rate based on a determination that the urgency level for the advertising data packet corresponds to a defined event associated with the data. In some embodiments, the modulating the beaconing rate for the advertising data packet can include decreasing the beaconing rate based on a determination that a communication connection is established between the medical device and an external device.

In yet another embodiment, an apparatus is provided. In some embodiments, the apparatus can be an external device. The apparatus can include a memory that stores executable components; and a processor coupled to the memory and configured to execute the executable components stored in the memory. The executable components can include a user feedback component and a communication component. The user feedback component can be configured to process user input data received via the apparatus. The communication component can be configured to transmit the user input data to a medical device via a first communication channel. The communication component can also be configured to scan for an advertising data packet via a second communication channel. A beaconing rate for the advertising data packet can be configured based on the user input data.

In some embodiments, the communication component can be configured to communicate with the medical device via a third communication channel based on a determination that the advertising data packet satisfies a defined criterion. In some embodiments, the user feedback component can be further configured to receive, via the apparatus, data that includes the beaconing rate. In other embodiments, the user feedback component can be further configured to receive, via the apparatus, data that includes an interval of time for broadcasting the advertising data packet.

In one or more additional embodiments, a non-transitory computer readable medium is provided that includes computer executable instructions that, based on execution, cause an implantable device including at least one processor to perform various operations. The operations can include determining a classification for data associated with the medical device. The operations can further include adjusting polling associated with an advertising data packet provided by the medical device based on the classification for the data.

In some embodiments, the operations can further include determining an urgency level for the advertising data packet based on the classification for the data. In some embodiments, the adjusting can include increasing or decreasing a defined beaconing rate for the advertising data packet.

In yet another embodiment, a system includes a medical device and a device. The medical device can include a classification component and a communication component. The classification component can be configured to determine a classification for data included in an advertising data packet associated with a telemetry communication protocol. The communication component can be configured to modulate the advertising data packet at a defined beaconing rate based on the classification for the data. The device can be configured to perform telemetry communication with the medical device using the telemetry communication protocol and the advertising data packet.

In some embodiments, the classification component can be configured to determine an urgency level for the advertising data packet based on the classification for the data. In some embodiments, the communication component can be further configured to modulate the advertising data packet at the defined beaconing rate based on the urgency level for the advertising data packet. In some embodiments, the communication component is configured to broadcast the advertising data packet at the defined beaconing rate based on the classification for the data.

Other embodiments and various non-limiting examples, scenarios and implementations are described in more detail below. The following description and the drawings set forth certain illustrative embodiments of the specification. These embodiments are indicative, however, of but a few of the various ways in which the principles of the specification may be employed. Other advantages and novel features of the embodiments described will become apparent from the following detailed description of the specification when considered in conjunction with the drawings.

DETAILED DESCRIPTION

The following detailed description is merely illustrative and is not intended to limit embodiments and/or application or uses of embodiments. Furthermore, there is no intention to be bound by any expressed or implied information presented in the preceding Technical Field, Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Additionally, the following description refers to components being "connected" and/or "coupled" to one another. As used herein, unless expressly stated otherwise, the terms "connected" and/or "coupled" mean that one component is directly or indirectly connected to another component, mechanically, electrically, wirelessly, inductively or otherwise. Thus, although the figures may depict example arrangements of components, additional and/or intervening components may be present in one or more embodiments.

Figure 1:
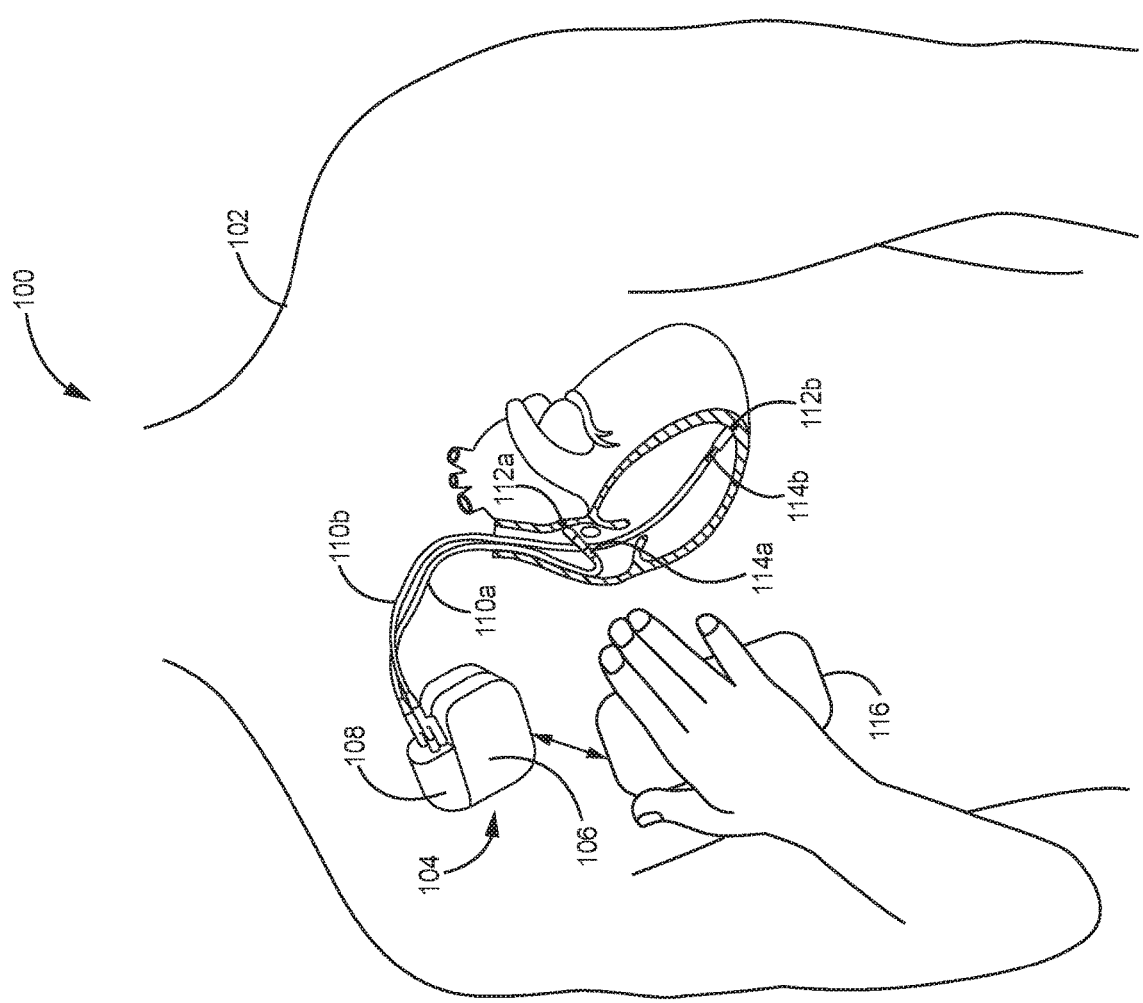
FIG. 1 illustrates a schematic diagram of an example, non-limiting medical device telemetry system facilitating improved telemetry between a medical device and an external device in accordance with one or more embodiments described herein.

With reference now to the drawings, FIG. 1 illustrates a schematic diagram of an example, non-limiting medical device telemetry system 100 facilitating improved telemetry between a medical device and an external device in accordance with one or more embodiments described herein. In the embodiment shown, medical device telemetry system 100 includes a medical device 104 associated with a body 102, and an external device 116. In some embodiments, as shown, the medical device 104 can be an IMD that is implanted within the body 102. However, in another embodiment, the medical device 104 can be an instrument that is employed externally from or on the body 102. In yet another example, the medical device 104 can be separate from an IMD (not shown in this embodiment) that is also implanted within the body 102 and communicatively and/or electrically coupled to the IMD. Embodiments of devices, apparatus and systems herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. In some embodiments, the medical device 104 can be configured to facilitate one or more diagnostic functions or treatment functions relative to the body 102.

One or more embodiments of medical device telemetry system 100 are described in connection with facilitating telemetry between the medical device 104 and the external device 116. The medical device 104 can communicate with the external device 116 using an advertising data packet. In an embodiment, the medical device 104 can communicate with the external device 116 based on a modulated beaconing rate for an advertising data packet. For instance, a rate for repeatedly broadcasting an advertising data packet can be varied. In one example, an advertising data packet broadcasted at a first beaconing rate can be modified to broadcast at a second beaconing rate. In some embodiments, the beaconing rate for an advertising data packet can be modulated based on an urgency level for the advertising data packet. In certain embodiments, a "beaconing rate" can be referred to as a "telemetry rate".

In one embodiment, the urgency level can be determined based on a classification of data associated with the medical device 104. For instance, the urgency level can be determined based on a classification for data generated by the medical device 104 and/or data employed by the medical device 104. In one example, classification for the data can include identifying a type of the data, assigning the data to a group, identifying one or more characteristics of the data, determining a value of the data, and/or determining whether the data satisfies a defined threshold.

In another embodiment, the urgency level can be selected from a set of urgency levels that includes different types of urgency levels. The set of urgency levels can, in one example, include a first urgency level (e.g., a low urgency level) associated with a first beaconing rate, a second urgency level (e.g., a moderate urgency level) associated with a second beaconing rate, and a third urgency level (e.g., an immediate urgency level) associated with a third beaconing rate. However, it is to be appreciated that the set of urgency levels can include any number of different urgency levels.

In some embodiments, the medical device 104 can be configured to detect the different types of urgency levels in the set of urgency levels. The medical device 104 can also modify a beaconing rate of an advertising data packet in correspondence to the urgency. Accordingly, different beaconing rates can correspond to different levels of urgency.

In an embodiment, the data associated with the medical device 104 can be included in the advertising data packet. An advertising data packet generated by the medical device 104 can be a data packet employed for advertising information to other devices (e.g., the external device 116). For example, the medical device 104 can broadcast certain data to share with other devices (e.g., the external device 116) via an advertising data packet. In one example, an advertising data packet can include the classified data to facilitate transmission of the classified data to other devices (e.g., the external device 116).

An advertising packet can include one or more types or sections of data that include information for other devices in close proximity to the medical device 104 that broadcasts the advertising data packet. For instance, an advertising data packet can include the classified data associated with the medical device 104. The classified data can be the data classified by the medical device 104, the data generated by the medical device 104 and/or the data received by the medical device 104. Therefore, the classified data associated with the medical device 104 can be shared with the other devices (e.g., the external device 116).

In an aspect, an advertising data packet can facilitate a connection between the medical device 104 and the external device 116 that receives the advertising data packet. In certain embodiments, the advertising data packet can include a header portion and a data portion that can be read by other devices (e.g., the external device 116) to determine whether the other devices should connect to the medical device 104. For example, the other devices (e.g., the external device 116) can establish a connection with the medical device 104 in response to a determination that the header portion includes information relevant to the other devices (e.g., the external device 116). However, the other devices (e.g., the external device 116) can withhold from establishing a connection with the medical device 104 in response to a determination that the header portion does not include information relevant to the other devices (e.g., the external device 116).

The medical device 104 can include one or more devices, transducers and/or circuits that can convert information from one format to another format. In some embodiments, the medical device 104 can include a device, a transducer and/or a circuit that can convert a signal associated with particular data for the medical device 104 (or, in embodiments in which the medical device 104 is an IMD, alternatively or additionally, the status of the IMD) to information for transmission by the medical device 104 (or generally to another signal of any number of different formats suitable for reception by the external device 116). The medical device 104 can also include one or more power supplies. For instance, the medical device can include a battery that supplies power to the one or more devices, transducers and/or circuits.

A beaconing rate of the advertising data packet broadcasted by the medical device 104 can be dynamically modified from time to time and/or based on one or more conditions. For example, an advertising data packet broadcasted by the medical device 104 can be associated with dynamic telemetry polling where a beaconing rate of the advertising data packet can be varied.

In an embodiment, a beaconing rate of the advertising data packet can vary based on the data associated with the medical device 104 (e.g., the classified data associated with the medical device 104) and/or the advertising data packet. For example, a beaconing rate of the advertising data packet can vary based on medical data associated with the medical device 104, remote monitoring data associated with the medical device 104, patient data associated with the medical device 104 or other data associated with the medical device 104. In an aspect, a beaconing rate for an advertising data packet that includes medical data can be determined based on a particular classification and/or urgency level for the medical data. In another aspect, a beaconing rate for an advertising data packet that includes remote monitoring data can be determined based on a particular classification and/or urgency level for the remote monitoring data. In yet another aspect, a beaconing rate for an advertising data packet that includes patient data can be determined based on a particular classification and/or urgency level for the patient data. In certain embodiments, transmission power associated with the advertising data packet can additionally or alternatively be modified based on a particular classification and/or urgency level for the medical data. For instance, the advertising data packet can be transmitted at a first transmission power level based on a first classification and/or a first urgency level for the medical data, and the advertising data packet can be transmitted at a second transmission power level based on a second classification and/or a second urgency level for the medical data. In one example, the second transmission power level can be less than the first transmission power level. Alternatively, the second transmission power level can be greater than the first transmission power level. Medical data can include medical data read or otherwise obtained by the medical device 104 (e.g., cardiac monitoring data, pacemaker monitoring data, glucose monitoring data, etc.), electrical signals sensed and/or generated by the medical device 104, a voltage or current provided by the medical device 104 and/or a medical dosage provided by the medical device 104. Patient data can include, for example, a name of a patient, a date of birth of a patient, a medical history associated with a patient, a medical identification or number associated with the patient or the like. Remote monitoring data can include, for example, analysis data associated with the medical device 104 and/or a patient, monitoring data for a condition associated with the medical device 104 and/or the body 102 of the patient, etc.

In another embodiment, a beaconing rate of the advertising data packet can vary based on type of data being monitored by the medical device 104. For example, a beaconing rate for the advertising data packet can be increased or decreased in response to a determination that a particular type of data is being monitored by the medical device 104. In a non-limiting example, a beaconing rate for the advertising data packet can be increased or decreased in response to a determination that a particular medical data (e.g., a particular cardiac data) is being monitored by the medical device 104. Additionally or alternatively, a beaconing rate of the advertising data packet can vary based on a determined reason for monitoring data associated with the medical device 104. For example, a beaconing rate for the advertising data packet can be increased or decreased in response to a determination that a particular condition for a patient is being monitored by the medical device 104. In a non-limiting example, a beaconing rate for the advertising data packet can be increased or decreased in response to a determination that a patient is being monitored for a particular type of medical condition via the medical device 104.

Additionally or alternatively, in certain embodiments, the medical device 104 can employ a fixed polling interval for broadcasting an advertising data packet and/or can adjust the fixed polling interval to allow for increased polling based on detection of a defined event associated with the medical device 104. For instance, the fixed polling interval can be related to a start time and a stop time for repeatedly broadcasting the advertising data packet. Moreover, a beaconing rate can be a rate for broadcasting an advertising data packet during the fixed polling interval. For example, an advertising data packet can be broadcasted at a particular frequency of occurrence during the fixed polling interval.

In one example, the fixed polling interval and/or a beaconing rate of an advertising data packet can be adjusted based on timestamp associated with an advertising data packet (e.g., based on a time of day associated with transmission of an advertising data packet) to facilitate synchronization of polling with respect to the medical device 104 and the external device 116. In another example, the fixed polling interval and/or a beaconing rate of an advertising data packet can be adjusted based on feedback data provided by the external device 116 (e.g., a physician associated with the external device 116 can adjust the fixed polling interval and/or a beaconing rate of an advertising data packet based on longevity tradeoff). In certain embodiments, the medical device 104 and/or the external device 116 can provide a patient (e.g., a patient associated with the body 102) with information related to timing for an expected connection between the medical device 104 and the external device 116 based on other information related to a last successful connection between the medical device 104 and the external device 116.

In an aspect, the medical device 104 can insert the data associated with the medical device 104 (e.g., medical data, remote monitoring data, patient data, etc.) into the advertising data packet. For example, the medical device 104 can generate data associated with the medical device 104. In some embodiments, generating the data can include can encoding the data associated with the medical device 104 into the advertising data packet.

The medical device 104 can also broadcast the advertising data packet at a defined beaconing rate determined based on the data associated with the medical device 104 (e.g., medical data, remote monitoring data, patient data, etc.). For example, the medical device 104 can broadcast the advertising data packet at a defined beaconing rate during a defined interval of time. As such, in some embodiments, the external device 116 can be provided an opportunity to receive the advertising data packet during the defined interval of time.

In a non-limiting example, the medical device 104 can broadcast an advertising data packet at a first defined beaconing rate. For example, the first defined beaconing rate can be a defined number of times per defined time period (e.g., once or twice per day). The first defined beaconing rate can be based on a determination that the medical device is not associated with an urgent condition associated with a particular urgency level or an urgent event associated with a particular urgency level.

Furthermore, the medical device 104 can broadcast an advertising data packet at a second defined beaconing rate (e.g., once or twice per hour) based on a determination that the medical device is associated with a medium urgency condition associated with a particular urgency level or a medium urgency event associated with a particular urgency level such as, for example, a sustained atrial fibrillation episode.

The medical device 104 can alternatively broadcast an advertising data packet at a third defined beaconing rate (e.g., continuously) based on a determination that the medical device is associated with an immediate urgency condition associated with a particular urgency level or an immediate urgency event associated with a particular urgency level such as, for example, a ventricular tachycardia episode, a ventricular fibrillation episode, critically low blood sugar, a myocardial infarction, or another type of medical condition critical to well being of the body 102. In an embodiment, the medical device 104 can return a beaconing rate for an advertising data packet to a slower rate based on a determination that a connection is established with the external device 116 and/or that data is successfully transferred to the external device 116.

The external device 116 can scan for the advertising data packet associated with the medical device 104 (e.g., without connecting to the medical device 104). For example, the external device 116 can include a receiver that can monitor for the advertising data packet generated by the medical device 104. As such, if the external device 116 is within a certain range from the medical device 104 and detects the advertising data packet, the external device 116 can obtain the data associated with the medical device 104 without connecting to the medical device 104.

In some embodiments, the external device 116 can establish a communication link with the medical device 104 based on the advertising data packet. For instance, the advertising data packet can include information indicative of a request to establish the communication link with the medical device 104. In one example, the advertising data packet can include an identifier for a particular communication channel. In another example, the advertising data packet can include an identifier for network device associated with a particular communication channel.

After establishment of the communication link between the medical device 104 and the external device 116, in some embodiments, the external device 116 and the medical device 104 can exchange one or more data packets. For example, after a communication link is established between the external device 116 and the medical device 104 (e.g., based on detection by the external device 116 of an advertising data packet that includes data associated with the medical device 104), the external device 116 can communicate with the medical device 104 to exchange data with the medical device 104. In a non-limiting example, the external device 116 can read data captured by the medical device 104 (e.g., electrogram data, etc.) during the communication. The medical device 104 can also transmit sensed physiological data, diagnostic determinations made based on the sensed physiological data, medical device 104 performance data and/or medical device 104 integrity data to the external device 116.

By employing the beaconing rate that is determined based on the classification of the data associated with the medical device 104, performance of the power supply (e.g., the one or more power sources, the battery) included in the medical device 104 can be improved. For instance, frequency of connections and/or number of unnecessary connections between the medical device 104 and the external device 116 can be reduced by employing the dynamic beaconing rate, thereby conserving power of the power supply (e.g., the one or more power sources, the battery) of the medical device 104. Moreover, data associated with the medical device 104 can be indicated to an external device using minimal power consumption, e.g., by not requiring a communication session to be established by the medical device 104 to receive information, but instead dynamically transmitting the data associated with the medical device 104 within the advertising packet. Further, in some embodiments, the processor and/or memory operations of the medical device 104 and/or the external device 116 can operate more efficiently due to reduction in processes for unnecessary connections between the external device 116 and the medical device 104.

Data associated with the medical device 104 can also be provided to a wide variety of external devices, including, but not limited to, a tablet computer associated with a patient or a physician, a smart phone associated with a patient or a physician, a medical device associated with a patient or a physician, an electronic device at a home of a patient or at an office of a physician, an off-the-shelf device purchased at a store, etc. Additionally, in some embodiments, compatibility between the medical device 104 and external devices can be increased by allowing the data associated with the medical device 104 to be included in an advertising data packet that can be received by any external device through the utilization of a communication protocol, such as, but not limited to, the BLUETOOTH® low energy communication protocol.

In the example shown in medical device telemetry system 100, a person operating the external device 116 can be a patient in which the medical device 104 is implanted. In another example, another person (e.g., such as medical caregiver) interacting with the patient in which the medical device 104 is implanted can operate the external device 116 outside the body 102 in which the medical device 104 is located. In various embodiments, the medical device 104 can include any number of different types of medical devices configured to communicate with the external device 116 or another external device. The particular, size, shape, placement and/or function of the medical device 104 may not be critical to the subject disclosure in some embodiments.

In one embodiment, as mentioned, the medical device 104 is or includes an IMD. For example, some example IMDs can include, but are not limited to, cardiac pacemakers, cardiac defibrillators, cardiac re-synchronization devices, cardiac monitoring devices, cardiac pressure monitoring devices, spinal stimulation devices, neural stimulation devices, gastric stimulation devices, diabetes pumps, drug delivery devices, and/or any other medical devices. In various embodiments, however, the medical device 104 can be or include any number of other types of implantable devices that are not IMDs.

For exemplary purposes, the medical device 104 is illustrated in medical device telemetry system 100 as an IMD implanted within the chest of a patient and configured to provide medical treatment associated with a heart disease or condition (e.g., an implantable cardioverter-defibrillator (ICD) and/or a pacemaker). In addition to the medical treatment, the medical device 104 can also be configured to provide the data packetizing and communication operations described herein. The medical device 104 includes a housing 106 within which electrical components and one or more power sources are housed. The electrical components can be powered via the one or more power sources. A power source (not shown) can include, but is not limited to, a battery, a capacitor, a charge pump, a mechanically derived power source (e.g., microelectromechanical systems (MEMs) device), or an induction component. The various embodiments described herein can provide improved management of power associated with the one or more power sources.

The electrical components can vary depending on the particular features and functionality of the medical device 104. In various embodiments, these electrical component can include, but are not limited to, one or more processors, memories, transmitters, receivers, transceivers, sensors, sensing circuitry, therapy circuitry, antennas and other components. In an embodiment, the electrical components can be formed on or within a substrate that is placed inside the housing 106. The housing 106 can be formed from conductive materials, non-conductive materials or a combination thereof. For example, housing 106 can include a conductive material, such as metal or metal alloy, a non-conductive material such as glass, plastic, ceramic, etc., or a combination of conductive and non-conductive materials. In some embodiments, the housing 106 can be a biocompatible housing (e.g., a liquid crystal polymer, etc.).

In the embodiment shown, the medical device 104 is also an IMD and further includes leads 110a,b connected to the housing 106. The leads 110a,b extend into the heart and respectively include one or more electrodes. For example, as depicted in medical device telemetry system 100, leads 110a,b each include a respective tip electrodes 112a,b and ring electrodes 114a,b located near a distal end of their respective leads 110a,b. When implanted, tip electrodes 112a,b and/or ring electrodes 114a,b are placed relative to or in a selected tissue, muscle, nerve or other location within the body 102 of the patient. As depicted in medical device telemetry system 100, tip electrodes 112a,b are extendable helically shaped electrodes to facilitate fixation of the distal end of leads 110a,b to the target location within the body 102 of the patient. In this manner, tip electrodes 112a,b are formed to define a fixation mechanism. In other embodiments, one or both of tip electrodes 112a,b may be formed to define fixation mechanisms of other structures. In other instances, leads 110a,b may include a fixation mechanism separate from tip electrodes 112a,b. Fixation mechanisms can be any appropriate type, including a grapple mechanism, a helical or screw mechanism, a drug-coated connection mechanism in which the drug serves to reduce infection and/or swelling of the tissue, or other attachment mechanism.

Leads 110a,b are connected at a proximal end of the medical device 104 via connector block 108. Connector block 108 may include one or more receptacles that interconnect with one or more connector terminals located on the proximal end of leads 110a,b. Leads 110a,b are ultimately electrically connected to one or more of the electrical components within housing 106. One or more conductors (not shown) extend within leads 110a,b from connector block 108 along the length of the lead to engage the ring electrodes 114a,b and tip electrodes 112a,b, respectively. In this manner, each of tip electrodes 112a,b and ring electrodes 114a,b is electrically coupled to a respective conductor within its associated lead bodies. For example, a first electrical conductor can extend along the length of the body of lead 110a from connector block 108 and electrically couple to tip electrode 112a and a second electrical conductor can extend along the length of the body of lead 110a from connector block 108 and electrically couple to ring electrode 114a. The respective conductors may electrically couple to circuitry, such as a therapy module or a sensing module, of the medical device 104 via connections in connector block 108.

In one or more embodiments, the medical device 104 is configured to deliver therapy to the heart (or other location) via the electrical conductors to one or more of electrodes 112a,b and 114a,b. In the case of pacing therapy, for example, the medical device 104 may deliver pacing pulses via a unipolar electrode configuration, e.g., using electrodes 112a,b and a housing electrode of the medical device 104. In other instances, the medical device 104 may deliver pacing pulses via a bipolar electrode configuration, e.g., using electrodes 112a,b and ring electrodes 114a,b. Medical device 104 may also receive sensed electrical signals on the electrical conductors from one or more of electrodes 112a,b and 114a,b. The medical device 104 may sense the electrical signals using either a unipolar or bipolar electrode configuration.

The configuration, features and functionality of medical device 104 are merely provided as an example. In other examples, the medical device 104 can include more or fewer leads extending from the housing 106. For example, the medical device 104 can be coupled to three leads, e.g., a third lead implanted within a left ventricle of the heart of the patient. In another example, the medical device 104 can be coupled to a single lead that is implanted within the ventricle of the heart of the patient. In other embodiments, the lead may be an extravascular lead with the electrodes implanted subcutaneously above the ribcage/sternum or underneath or below the sternum. Example extravascular ICDs having subcutaneous electrodes are described in U.S. Patent Publication No. 2014/0214104 (Greenhut et al.) and U.S. Patent Publication No. 2015/0133951 (Seifert et al.), each of which is incorporated herein in its entirety. One example extravascular ICD having substernal electrodes is described in U.S. Patent Publication No. 2014/0330327 (Thompson-Nauman et al.). In some embodiments, the medical device 104 can include other leads (e.g., atrial lead and/or left ventricular lead). As such, medical device 104 can be used for single chamber or multi-chamber cardiac rhythm management therapy. In addition to more or fewer leads, each of the leads may include more or fewer electrodes. In instances in which the medical device 104 is used for therapy other than pacing, (e.g., defibrillation or cardioversion), the leads can include elongated electrodes, which may, in some instances, take the form of a coil. The medical device 104 can deliver defibrillation or cardioversion shocks to the heart via any combination of the elongated electrodes and housing electrode. As another example, the medical device 104 can include leads with a plurality of ring electrodes, (e.g., as used in some implantable neurostimulators), without a tip electrode or with one of the ring electrodes functioning as the "tip electrode."

In another embodiment, the medical device 104 may include no leads, as in the case of an intracardiac pacemaker or a leadless pressure sensor. In the case of an intracardiac pacemaker, the device may include a housing sized to fit wholly within the patient's heart. In one example, the housing may have a volume that is less than 1.5 cc and, more preferably, less than 1.0 cubic centimeter (cc). However, the housing may be greater than or equal to 1.5 cc in other examples. The intracardiac pacemaker includes at least two electrodes spaced apart along the outer portion of the housing for sensing cardiac electrogram signals and/or delivering pacing pulses. Example intracardiac pacemakers are described in commonly-assigned U.S. Patent Publication No. 2012/0172690 (Anderson et al.), U.S. Patent Publication No. 2012/0172941 (Kenneth), and U.S. Patent Publication No. 2014/0214104 (Greenhut et al.), each of which is incorporated herein in its entirety. In the case of a leadless pressure sensor, the device may include a housing having a fixation member and a pressure sensing component. One example of a leadless pressure sensor is described in U.S. Patent Publication No. 2012/0108922 (Schell et al.), which is incorporated herein in its entirety.

External device 116 can include any suitable computing device configured to communicate with medical device 104. In some embodiments, the external device 116 can be a remote electronic device. For example, external device 116 can include, but is not limited to, a handheld computing device, a mobile phone, a smart phone, a tablet personal computer (PC), a laptop computer, a desktop computer, a personal digital assistant (PDA) and/or a wearable device. In some embodiments, the external device 116 can include a display that can present data associated with the medical device 104. In another embodiment, the external device 116 can include an application and/or a program associated with the medical device 104.

Figure 2:
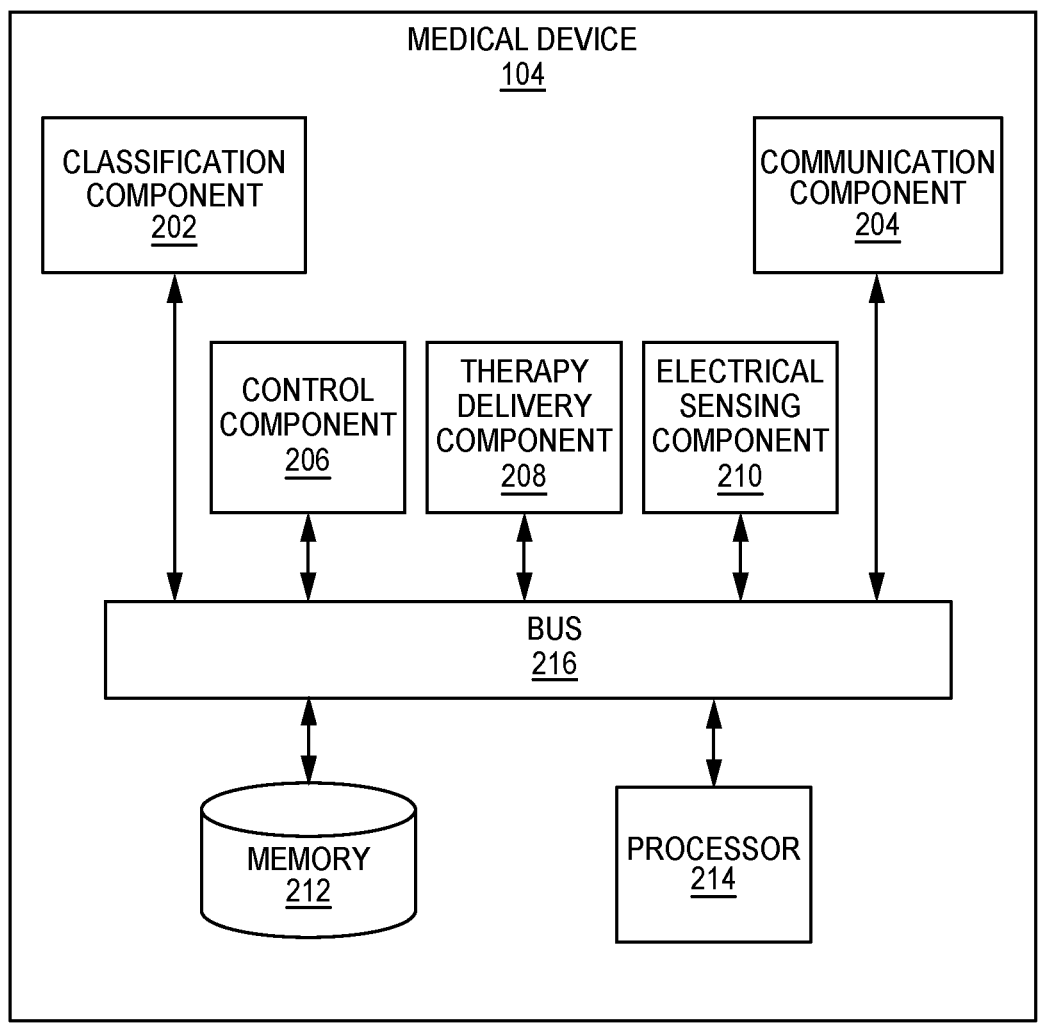
FIG. 2 illustrates a block diagram of an example, non-limiting medical device in accordance with one or more embodiments described herein.

FIG. 2 illustrates a block diagram of an example, non-limiting medical device (e.g., medical device 104) in accordance with one or more embodiments described herein. The medical device 104 includes a classification component 202, a communication component 204, a control component 206, a therapy delivery component 208 and/or an electrical sensing component 210. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Medical device 104 can include a memory 212 for storing computer executable components and instructions. Medical device 104 can further include a processor 214 to facilitate operation of the instructions (e.g., computer executable components and instructions) by medical device 104. Medical device 104 can also include a bus 216 that couples the various components of the medical device 104, including, but not limited to, the classification component 202, the communication component 204, the control component 206, the therapy delivery component 208, the electrical sensing component 210, the memory 212 and/or the processor 214. Repetitive description of like elements employed in other embodiments described herein is omitted for sake of brevity.

In some embodiments, one or more of the classification component 202 and/or the communication component 204 of the medical device 104 can facilitate a reduction in current employed by the medical device 104 while increasing likelihood of a connection with the external device 116. For instance, the classification component 202 and/or the communication component 204 of the medical device 104 can be employed to determine an appropriate beaconing rate for an advertising data packet broadcasted by the medical device 104 based on a classification of data associated with the advertising data packet and/or the medical device 104. In an embodiment, the classification component 202 can determine a classification for data associated with the medical device 104. For instance, the classification component 202 can determine a classification for data generated by the medical device 104. Data generated by the medical device 104 can include, for example, medical data generated by the medical device 104, remote monitoring data generated by the medical device 104, patient data generated by the medical device 104, status data generated by the medical device 104 and/or other data generated by the medical device 104. Medical data can include medical data read or otherwise obtained by the medical device 104, electrical signals sensed and/or generated by the medical device 104, a voltage or current provided by the medical device 104 and/or a medical dosage provided by the medical device 104. Remote monitoring data can include, for example, analysis data associated with the medical device 104 and/or a patient, monitoring data for a condition associated with the medical device 104 and/or the body 102 of the patient. Patient data can include, for example, a name of a patient, a date of birth of a patient, a medical history associated with a patient, a medical identification or number associated with the patient or the like. Status data can include, for example, a status of the medical device 104 (e.g., a particular mode of the medical device 104, a particular type of processing being performed by the medical device, a particular type of data being processed by the medical device 104, etc.), a processing status of the medical device 104 (e.g., a completion percentage for processing performed by the medical device 104, a performance characteristic of processing by the medical device, etc.), a power status of the medical device 104 (e.g., a powered-on state of the medical device 104, a powered-off state of the medical device, longevity information for a power source of the medical device 104, a power capacity of a power source of the medical device 104, etc.), a software version status of the medical device 104, a status of component(s) included in the medical device 104 or the like. Additionally or alternatively, the classification component 202 can determine a classification for data received by the medical device 104. Data received by the medical device 104 can include, for example, medical data received by the medical device 104, remote monitoring data received by the medical device 104, patient data received by the medical device 104, status data received by the medical device 104 and/or other data received by the medical device 104.

The classification component 202 can also determine an urgency level for an advertising data packet generated and/or broadcasted by the medical device 104. The classification component 202 can determine an urgency level for an advertising data packet based on the classification for the data. In certain embodiments, the classification component 202 can additionally or alternatively determine a defined event or a defined condition associated with the data. For instance, the classification component 202 can determine whether the data satisfies a defined criterion that corresponds to a defined event or a defined condition. In an aspect, an urgency level for an advertising data packet can correspond to a defined event associated with the medical device 104. A defined event or a defined condition can be, for example, a defined medical event associated with the data generated by the medical device 104. In one example, a defined medical event can be associated with a cardiac rhythm reading for physiological data sensed by the medical device 104. In another example, a defined medical event can be associated with sensed electrical signals on electrical conductors from the one or more of electrodes 112a,b and 114a,b. Additionally or alternatively, a defined event can be a processing event associated with the medical device 104. For instance, a processing event associated with the medical device 104 can be related to processing performance of one or more components included in the medical device 104. Processing performance can include, for example, a number of processing cycles performed by the one or more components included in the medical device 104, voltage levels for the one or more components included in the medical device 104, current levels for the one or more components included in the medical device 104, etc.

In one example, the classification component 202 can determine the data associated with the medical device 104 via one or more components of the medical device 104 and/or one or more components in communication with the medical device 104. For example, in an implementation, the classification component 202 can retrieve data associated with the medical device 104 from memory (e.g., memory 212), the control component 206 or the electrical sensing component 210. In another example, the classification component 202 can receive data associated with the medical device 104 from another component included in the medical device 104. By way of example, but not limitation, a detection component of an IMD, for example, can detect and/or read one or more signals or other measurement data that can then be obtained by the classification component 202.

The communication component 204 can be configured to generate and/or broadcast an advertising data packet associated with the medical device 104. In an embodiment, the communication component 204 can broadcast an advertising data packet for the medical device 104 at a defined beaconing rate based on the urgency level for the advertising data packet that is determined by the classification component 202. For instance, the communication component 204 can broadcast the advertising data packet via modulation of the broadcast at the defined beaconing rate. The communication component 204 can, for example, modify the defined beaconing rate from a first defined beaconing rate to a second defined beaconing rate. For instance, the communication component 204 can increase the defined beaconing rate based on a determination that the urgency level for the advertising data packet corresponds to a defined event associated with the data. Alternatively, the communication component 204 can decrease the defined beaconing rate based on a determination that the urgency level for the advertising data packet corresponds to a defined event associated with the data. In another example, the communication component 204 can decrease the defined beaconing rate based on a determination that a communication connection is established between the medical device 104 and the external device 116.

In an embodiment, the communication component 204 can modify the defined beaconing rate based on time data indicative of a timestamp associated with the broadcast of the advertising data packet. For instance, the communication component 204 can decrease the defined beaconing rate or increase the defined beaconing rate based on a timestamp associated with the broadcast of the advertising data packet by the medical device 104. In another embodiment, the communication component 204 can modify the defined beaconing rate based on time data indicative of a clock value for a clock associated with a processor (e.g., processor 214) of the medical device 104. For instance, the communication component 204 can modify the defined beaconing rate and/or transmit the advertising data packet at a defined time of day (e.g., increase a beaconing rate of the advertising data packet and/or begin transmitting the advertising at a defined beaconing rate at 5 pm, etc.). In one example, based on a determination that a time of day of the broadcast satisfies a defined criterion, the communication component 204 can decrease the defined beaconing rate. For instance, the communication component 204 can decrease the defined beaconing rate in the morning and/or increase the defined beaconing rate in the middle of the night.

In another embodiment, the communication component 204 can modify the defined beaconing rate based on historical data indicative of a history of data exchanges with respect to the external device 116. For example, the communication component 204 can modify the defined beaconing rate based on a history of previously successful connections between the medical device 104 and the external device 116. In yet another embodiment, the communication component 204 can modify the defined beaconing rate based on receipt of user input by the medical device 104. For instance, user input can be received by the external device 116 or an external device. The user input can be related to a defined beaconing rate for an advertising data packet and/or a defined interval of time for broadcasting an advertising data packet. In an aspect, the external device 116 or the other device associated with the user input can transmit data indicative of the user input to the medical device 104. In another aspect, the user input can include one or more priority schemes for an advertising data packet. For example, a user (e.g., a doctor, etc.) can employ the external device to set a different setting for the medical device 104. Based on the different setting associated with the user input, the classification component 202 can modify an urgency level for the advertising data packet.

In yet another embodiment, the communication component 204 can modify the defined beaconing rate based on longevity data indicative of a lifespan period for a battery of the medical device 104. For instance, a total number of advertising data packets and/or rate of advertising data packets broadcasted by the communication component 204 can be determined based on the longevity data.

In certain embodiments, the communication component 204 can modify transmission power associated with an advertising data packet for the medical device 104 based on the urgency level for the advertising data packet that is determined by the classification component 202. For instance, the communication component 204 can broadcast the advertising data packet at a first transmission power level based on a first urgency level for the advertising data packet that is determined by the classification component 202, and the communication component 204 can broadcast the advertising data packet at a second transmission power level based on a second urgency level for the advertising data packet that is determined by the classification component 202. In one example, the second transmission power level can be less than the first transmission power level. Alternatively, the second transmission power level can be greater than the first transmission power level.

In an aspect, the communication component 204 can include a packet generator, a transmitter, a frequency modulator, and/or other circuitry configured to generate the advertising data packet using the defined beaconing rate determined based on the urgency level for the advertising data packet. The advertising data packet can be configured for transmission over an advertising communication channel. In some embodiments, the advertising communication channel can be a communication channel that is associated with a particular frequency employed for broadcast of information. In various embodiments, the advertising communication channel described herein can be a 2402 megahertz (MHz) communication channel, a 2426 MHz communication channel and/or a 2480 MHz communication channel. The particular frequencies provided are mere examples and, in other embodiments, the advertising communication channel can be located at any number of other different frequencies.

The communication component 204 can wirelessly transmit the advertising data packet associated with the medical device 104. For instance, the communication component 204 can wirelessly transmit from the body 102 the advertising data packet associated with the medical device 104. In one example, the communication component 204 can transmit the advertising data packet that includes the data associated with the medical device 104 during a defined period of time. In another example, the communication component 204 can transmit the advertising data packet one or more times during a defined period of time to advertise the advertising data packet to an external device (e.g., the external device 116). In some embodiments, the communication component 204 can sequentially transmit the advertising data packet associated with the medical device 104 via two or more advertising communication channels. For example, the communication component 204 can sequentially transmit the advertising data packet via a first advertising communication channel (e.g., a 2402 MHz communication channel), a second advertising communication channel (e.g., a 2426 MHz communication channel) and/or a third advertising communication channel (e.g., a 2480 MHz communication channel). In another example, the communication component 204 can concurrently transmit the advertising data packet associated with the medical device 104 via two or more of the advertising communication channels. For example, the communication component 204 can concurrently transmit the advertising data packet that includes the data associated with the medical device 104 via a first advertising communication channel (e.g., a 2402 MHz communication channel), a second advertising communication channel (e.g., a 2426 MHz communication channel) and/or a third advertising communication channel (e.g., a 2480 MHz communication channel).

The communication component 204 can transmit the advertising data packet via an advertising communication channel associated with a communication protocol utilizing lower energy consumption than a conventional communication protocol for wirelessly transmitting data. In a non-limiting example, the communication component 204 can transmit the advertising data packet via an advertising communication channel associated with a BLUETOOTH® low energy (BLE) protocol. The communication component 204 can additionally or alternatively establish, via a communication channel that different than the advertising communication channel associated with the advertising data packet, a wireless communication link with the external device 116. Based on establishing the wireless communication link, the classification component 202 can modify the defined beaconing rate. For instance, the classification component 202 can reduce the defined beaconing rate for the advertising data packet based on a determination that the wireless communication link is established with the external device 116. In one embodiment, the medical device 104 can connect to (e.g., actively communicate with) the external device 116, transmit data directly to the external device 116 and/or receive data from the external device 116 via the wireless communication link. For example, the external device 116 can read data captured by the medical device 104 (e.g., electrogram data) via the wireless communication link. In another example, the medical device 104 can transmit sensed physiological data, diagnostic determinations made based on the sensed physiological data, medical device 104 performance data and/or medical device 104 integrity data to external device 116 via the wireless communication link.

With reference to FIGS. 1 and 2, in some embodiments, the control component 206 can communicate with the therapy delivery component 208 and/or the electrical sensing component 210. For example, the control component 206 can communicate with the therapy delivery component 208 and/or the electrical sensing component 210 to facilitate sensing of cardiac electrical activity, detection of cardiac rhythms, and generation of electrical stimulation therapies based on sensed signals. The therapy delivery component 208 can be, for example, electrically coupled to tip electrodes 112a,b, ring electrodes 114a,b and/or the housing 106 to deliver electrical stimulation therapies such as cardioversion-defibrillation (CV/DF) shocks. In some examples, the therapy delivery component 208 can be additionally coupled to tip electrodes 112a,b and/or ring electrodes 114a,b for use in delivering therapy and/or delivering mild electrical stimulation to generate a patient alert.

The electrical sensing component 210 can be electrically coupled to tip electrodes 112a,b and ring electrodes 114a,b carried by leads 110a,b and housing 106, which may serve as a common or ground electrode. The electrical sensing component 210 can be selectively coupled to tip electrodes 112a,b, ring electrodes 114a,b and/or the housing 106 in order to, for example, monitor electrical activity of the patient's heart (e.g., electrical activity associated with tip electrodes 112a,b and/or ring electrodes 114a,b). For example, the electrical sensing component 210 can include detection circuitry associated with tip electrodes 112a,b and/or ring electrodes 114a,b. In one embodiment, the electrical sensing component 210 can be enabled to monitor one or more sensing vectors selected from the tip electrodes 112a,b and/or the ring electrodes 114a,b. For example, the electrical sensing component 210 can include switching circuitry for selecting which of tip electrodes 112a,b, ring electrodes 114a,b and housing 106 are coupled to sense amplifiers or other cardiac event detectors included in the electrical sensing component 210. Switching circuitry can include, for example, a switch array, a switch matrix, a multiplexer, or any other type of switching device suitable to selectively couple sense amplifiers to selected electrodes.

In some examples, the electrical sensing component 210 can include multiple sensing channels for sensing multiple electrocardiogram (ECG) sensing vectors selected from tip electrodes 112a,b, ring electrodes 114a,b and/or the housing 106. For example, the electrical sensing component 210 can include two sensing channels. Each sensing channel can include a sense amplifier or other cardiac event detection circuitry for sensing cardiac events, e.g., R-waves, from the received ECG signal developed across selected electrodes (e.g., tip electrodes 112a,b and/or ring electrodes 114a,b). The cardiac event detector can operate using an auto-adjusting sensing threshold set based on a peak amplitude of a currently sensed event that can decay over time. Each time the received ECG signal crosses the auto-adjusting sensing threshold outside an absolute blanking period, a cardiac sensed event signal, such as an R-wave sensed event signal, can be produced and passed to the control component 206 for use in detecting ventricular tachycardia (VT).

The control component 206 can be configured, for example, to detect VT episodes that may be life-threatening if left untreated (generally referred to herein as a "shockable rhythm") such as, for example, non-sinus VT, ventricular fibrillation, etc. The timing of R-wave sensed event signals received from the electrical sensing component 210 can be used by the control component 206 to determine R wave to R wave intervals between cardiac sensed event signals. The control component 206 can, for example, count RR intervals that fall into different rate detection zones for determining a ventricular rate or performing other rate-based assessments or interval-based assessments for detecting VT and discriminating VT from rhythms that do not require a CV/DF shock.

The electrical sensing component 210 can additionally or alternatively include an analog-to-digital converter that provides a digital ECG signal from one or all available sensing channels to the control component 206 for further signal analysis for use in VT detection. A sensed ECG signal can be converted to a multi-bit digital signal by the electrical sensing component 210 and provided to the control component 206 for performing ECG morphology analysis. Analysis of the ECG signal morphology can be performed for detecting, confirming or discriminating VT.

In an embodiment, the therapy delivery component 208 can include a high voltage (HV) therapy delivery module including one or more HV output capacitors and, in some instances, a low voltage therapy delivery module. When a shockable VT rhythm is detected, the HV output capacitors can be charged to a predefined voltage level by a HV charging circuit. The control component 206 can, for example apply a signal to trigger discharge of the HV capacitors upon detecting a feedback signal from the therapy delivery component 208 that the HV capacitors have reached the voltage required to deliver a programmed shock energy. In this way, the control component 206 can control operation of the high voltage output circuit of the therapy delivery component 208 to deliver high energy cardiover-sion/defibrillation shocks using tip electrodes 112a,b, ring electrodes 114a,b and/or the housing 106.

Each sensing channel included in the electrical sensing component 210 can include spike detector circuitry for detecting non-physiological electrical signal spikes present in the cardiac electrical(s) received by the electrical sensing component 210. The spike detector can produce a spike detect signal passed to the control component 206 for use in detecting a lead issue as well as avoiding false detections of VT due to oversensing of electrical spikes that are not true R-waves. In some examples, the electrical sensing component 210 can be configured to detect pacing pulses delivered to the body 102. For example, bradycardia pacing pulses or anti-tachycardia pacing pulses delivered by the medical device 104 may be detected by the spike detector of the electrical sensing component 210.

Figure 3:
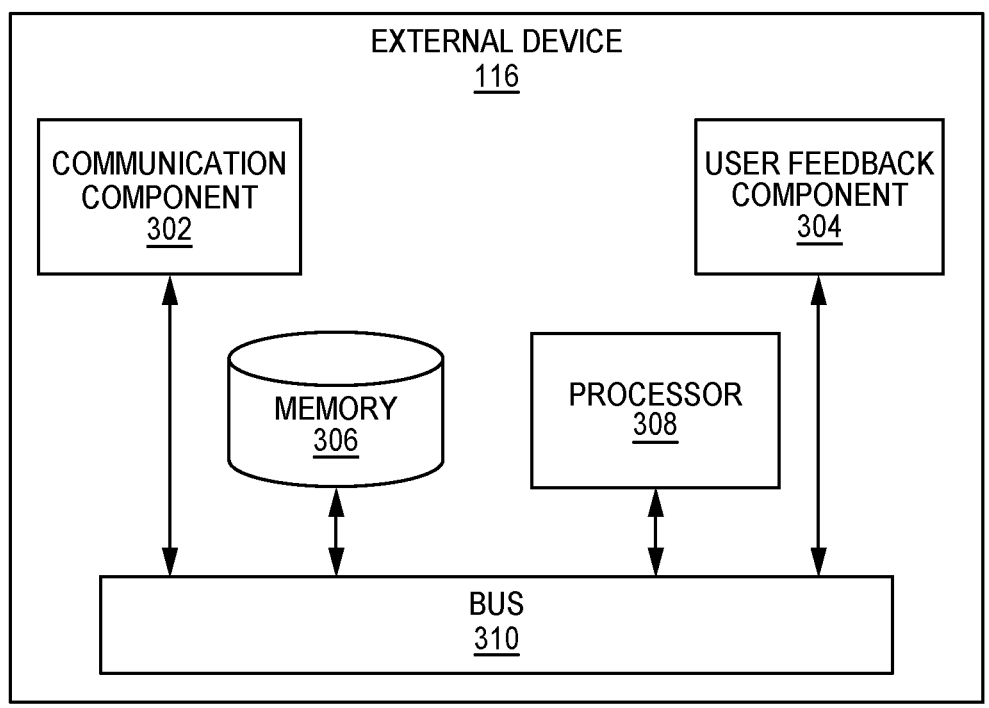
FIG. 3 illustrates a block diagram of an example, non-limiting external device in accordance with one or more embodiments described herein.

FIG. 3 illustrates a block diagram of an example, non-limiting external device (e.g., external device 116) in accordance with one or more embodiments described herein. The external device 116 includes a communication component 302 and a user feedback component 304. Aspects of the systems, apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. External device 116 can include memory 306 for storing computer executable components and instructions. External device 116 can further include a processor 308 to facilitate operation of the instructions (e.g., computer executable components and instructions) by external device 116. External device 116 can include a bus 310 that couples the various components of the external device 116, including, but not limited to, the communication component 302, the user feedback component 304, the memory 306 and/or the processor 308. Repetitive description of like elements employed in other embodiments described herein is omitted for sake of brevity.

The external device 116 can employ telemetry communication to communicate with one or more other devices such as, for example, the medical device 104. For example, the communication component 302 of the external device 116 can perform telemetry communication with other devices such as, for example, the medical device 104 using a telemetry communication protocol. In an embodiment, the communication component 302 can scan for an advertising data packet associated with a medical device (e.g., medical device 104) via at least one advertising communication channel. For example, the communication component 302 can passively scan an advertising data packet associated with a medical device (e.g., medical device 104) without transmitting data to the medical device 104. In various embodiments, the communication component 302 can scan a first advertising communication channel (e.g., a 2402 MHz communication channel), a second advertising communication channel (e.g., a 2426 MHz communication channel) and/or a third advertising communication channel (e.g., a 2480 MHz communication channel) for an advertising data packet associated with a medical device (e.g., medical device 104). In embodiments in which two or more channels are scanned, the particular advertising channels can be scanned in any order.

The communication component 302 can also establish a communication link with the medical device 104 via a communication channel that is different than the advertising communication channel based on a determination that a criterion associated with an identified advertising data packet is satisfied. A criterion associated with an identified advertising data packet can be, for example, that the identified advertising data packet is intended for and/or can be processed by the external device 116. For example, a criterion associated with an identified advertising data packet can be related to medical data associated with the medical device 104, remote monitoring data associated with the medical device 104, patient data associated with the medical device 104, status data associated with the medical device 104 and/or other data associated with the medical device 104

The user feedback component 304 can process user input that is received by the external device 116. The user input can be related to the medical device 104. For instance, the user input can be related to a defined beaconing rate for an advertising data packet associated with the medical device 104. Additionally or alternatively, the user input can be related to an interval of time for broadcasting an advertising data packet associated with the medical device 104.

In an embodiment, the user feedback component 304 can process user input data received via the external device 116. For example, the user feedback component 304 can determine a defined beaconing rate and/or a defined interval of time included in the user input data. In certain embodiments, the user feedback component 304 can analyze the user input data to determine a defined set of bits. In other embodiments, the user feedback component 304 can decode the user input data. The communication component 302 can transmit the processed user input data to the medical device 104 via a first communication channel (e.g., a first BTLE communication channel). Based on receiving the processed user input data, the medical device 104 (e.g., the communication component 204) can broadcast an advertising data packet based on the defined beaconing rate and/or a defined interval of time included in the user input data. For instance, the medical device 104 (e.g., the communication component 204) can broadcast the advertising data packet (e.g., the advertising data packet that is generated based on the defined beaconing rate and/or a defined interval of time included in the user input data) via a second communication channel (e.g., a second BTLE communication channel). Additionally, the communication component 204 can scan for the advertising data packet (e.g., the advertising data packet that is generated based on the defined beaconing rate and/or a defined interval of time included in the user input data) via the second communication channel. Based on identifying the advertising data packet via the second communication channel and/or a determination that the advertising data packet satisfies a defined criterion, the communication component 204 can communicate with the medical device 104 via a third communication channel. For example, the communication component 204 can communicate with the medical device 104 via a third communication channel based on a determination that the advertising data packet associated with the third communication channel includes particular data that is relevant to the external device 116.

Accordingly, power source consumption (e.g., battery power consumption) of the external device 116 and/or the medical device 104 can be reduced by employing a modulated beaconing rate for an advertising data packet associated with the medical device 104. A modulated beaconing rate for an advertising data packet associated with the medical device 104 can also provide improved longevity of the external device 116 and/or the medical device 104. Moreover, in some embodiments, compatibility with various external devices associated with a BLE protocol (e.g., off-the-shelf external devices associated with a BTLE protocol) can also be improved by employing a modulated beaconing rate for an advertising data packet associated with the medical device 104 and/or the external device 116.

Figure 4:
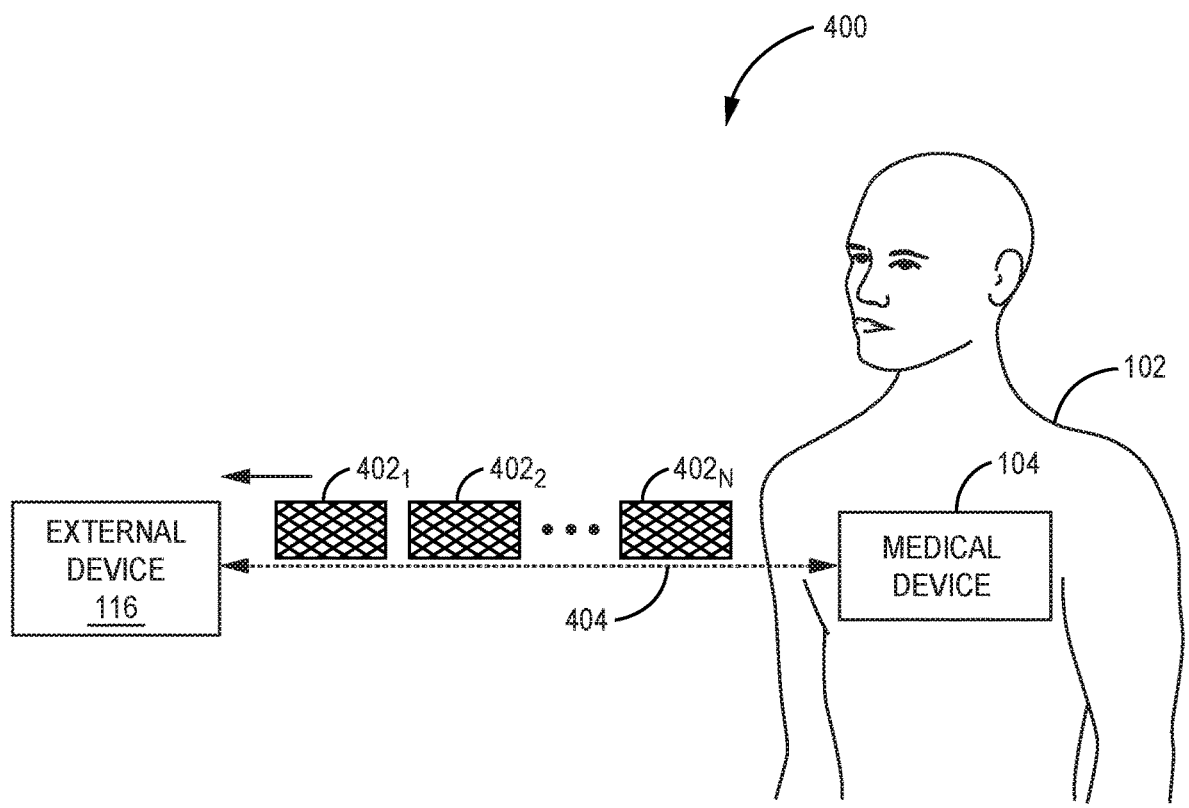
FIG. 4 illustrates an example, non-limiting medical device telemetry system facilitating telemetry between a medical device and an external device based on an advertising data packet in accordance with one or more embodiments described herein.

FIG. 4 illustrates an example, non-limiting medical device telemetry system facilitating telemetry between a medical device and an external device based on an advertising data packet in accordance with one or more embodiments described herein. Medical device telemetry system 400 includes the medical device 104 and the external device 116. Repetitive description of like elements employed in other embodiments described herein is omitted for sake of brevity.

The medical device 104 (e.g., the communication component 204) can generate an advertising data packet 402 that includes data associated with the medical device 104. The medical device 104 can also transmit or broadcast the advertising data packet 402 at a defined beaconing rate based on an urgency level for the advertising data packet that is determined by the classification component 202 and/or a classification for data included in the advertising data packet that is classified by the classification component 202. In one embodiment, the medical device 104 can repeatedly transmit the advertising data packet 402 as a first advertising data packet $402_1$, a second advertising data packet $402_2$, an Nth advertising data packet $402_N$, etc. during a defined period of time (e.g., a defined interval of time). For instance, the medical device 104 can transmit the first advertising data packet $402_1$ at a first defined time, the second advertising data packet $402_2$ at a second defined time, the Nth advertising data packet $402_N$ at an Nth defined time, etc. In an aspect, the defined beaconing rate can be formed based on, for example, an interval of time between the first defined time and the second defined time. The advertising data packet 402 can be communicated between the medical device 104 and the external device 116 via a low power communication protocol such as, for example, BLE.

The medical device 104 can transmit and/or broadcast the advertising data packets $402_{1-N}$ via an advertising communication channel 404. In one embodiment, the medical device 104 can repeatedly transmit the advertising data packet 402 as the advertising data packets $402_{1-N}$ via the advertising communication channel 404 during a defined period of time. A frequency of occurrence for repeatedly broadcasting the advertising data packets $402_{1-N}$ during the defined period of time can correspond to a defined beaconing rate determined by the classification component 202 and/or the communication component 204. For example, a rate for broadcasting the advertising data packets $402_{1-N}$ during the defined period of time can be determined based on data included in the advertising data packets $402_{1-N}$. In another embodiment, the advertising communication channel 404 shown in FIG. 4 can represent a set of advertising communication channels. For instance, the advertising data packet 402 can be broadcasted via the advertising communication channel 404 and one or more other advertising communication channels. In one example, the first advertising data packet $402_1$ can be broadcasted via a first advertising communication channel associated with the advertising communication channel 404, the second advertising data packet $402_2$ can be broadcasted via a second advertising communication channel associated with the advertising communication channel 404, the Nth advertising data packet $402_N$ can be broadcasted via an Nth advertising communication channel associated with the advertising communication channel 404. In one example, the advertising communication channel 404 can be an advertising channel associated with a BLE protocol. For example, the first advertising data packet $402_1$ can be transmitted as a first bit stream that is grouped into a set of code words, the second advertising data packet $402_2$ can be transmitted as a second bit stream that is grouped into the set of code words, the Nth advertising data packet $402_N$ can be transmitted as an Nth bit stream that is grouped into the set of code words, etc. In one example of the system 500, the medical device 104 can be implemented as an advertiser device and the external device 116 can be implemented as a scanner device.

Figure 5:
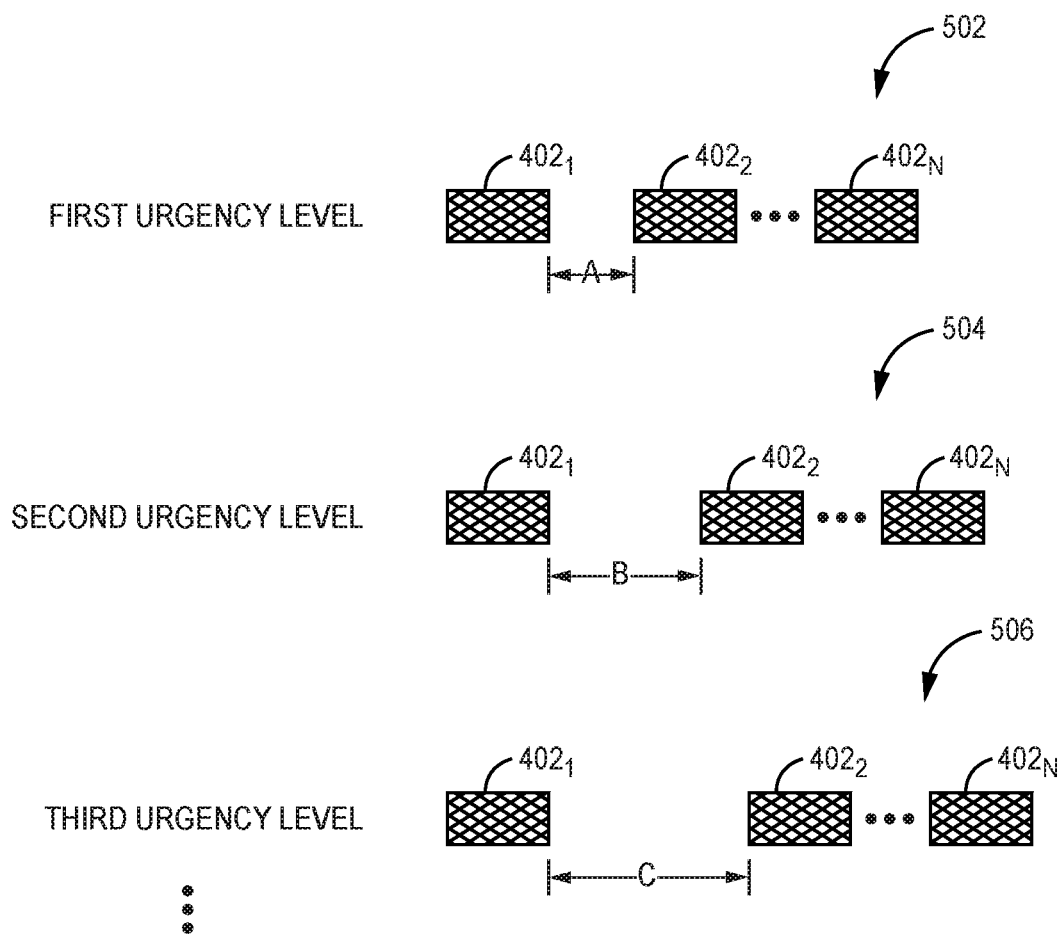
FIG. 5 illustrates example, non-limiting urgency modulated beaconing rates for a medical device telemetry system in accordance with one or more embodiments described herein.

FIG. 5 illustrates example, non-limiting urgency modulated beaconing rates for a medical device telemetry system in accordance with one or more embodiments described herein. In the embodiment shown in FIG. 5, a first polling process 502 illustrates broadcasting of the advertising data packets $402_{1-N}$ at a first defined beaconing rate, a second polling process 504 illustrates broadcasting of the advertising data packets $402_{1-N}$ at a second defined beaconing rate, and a third polling process 506 illustrates broadcasting of the advertising data packets $402_{1-N}$ at a third defined beaconing rate. The first polling process 502, the second polling process 504, and the third polling process 506 can be configured and/or generated by the classification component 202 and/or the communication component 204. It is to be appreciated that a medical device (e.g., the medical device 104) can be associated with a different number of defined beaconing rates for broadcasting the advertising data packets $402_{1-N}$.

During the first polling process 502, a time interval A between broadcasting, for example, the advertising data packet $402_1$ and the advertising data packet $402_2$ can be related to the first defined beaconing rate. Furthermore, during the second polling process 504, a time interval B between broadcasting, for example, the advertising data packet $402_1$ and the advertising data packet $402_2$ can be related to the second defined beaconing rate. During the third polling process 506, a time interval C between broadcasting, for example, the advertising data packet $402_1$ and the advertising data packet $402_2$ can be related to the third defined beaconing rate. The time interval A can be a first advertising interval, the time interval B can be a second advertising interval, and the time interval C can be a third advertising interval. As shown in FIG. 5, the first defined beaconing rate related to the time interval A can be more frequent than the second defined beaconing rate related to the time interval B and the third defined beaconing rate related to the time interval C. For instance, the first defined beaconing rate related to the time interval A can be associated with a higher frequency of occurrence than the second defined beaconing rate related to the time interval B and the third defined beaconing rate related to the time interval C. Moreover, the second defined beaconing rate related to the time interval B can be more frequent than the third defined beaconing rate related to the time interval C, but less frequent than the first defined beaconing rate related to the time interval A. The third defined beaconing rate related to the time interval C can be less frequent than the first defined beaconing rate related to the time interval A and the second defined beaconing rate related to the time interval B. In an embodiment, the first polling process 502 can be associated with a first urgency level, the second polling process 504 can be associated with a second urgency level, and the third polling process 506 can be associated with a third urgency level. For instance, the first urgency level can be related to an immediate urgency event associated with the medical device 104, the second urgency level can be related to a medium urgency event associated with the medical device 104, and the third urgency level can be related to a low urgency event associated with the medical device 104.

Figure 6:
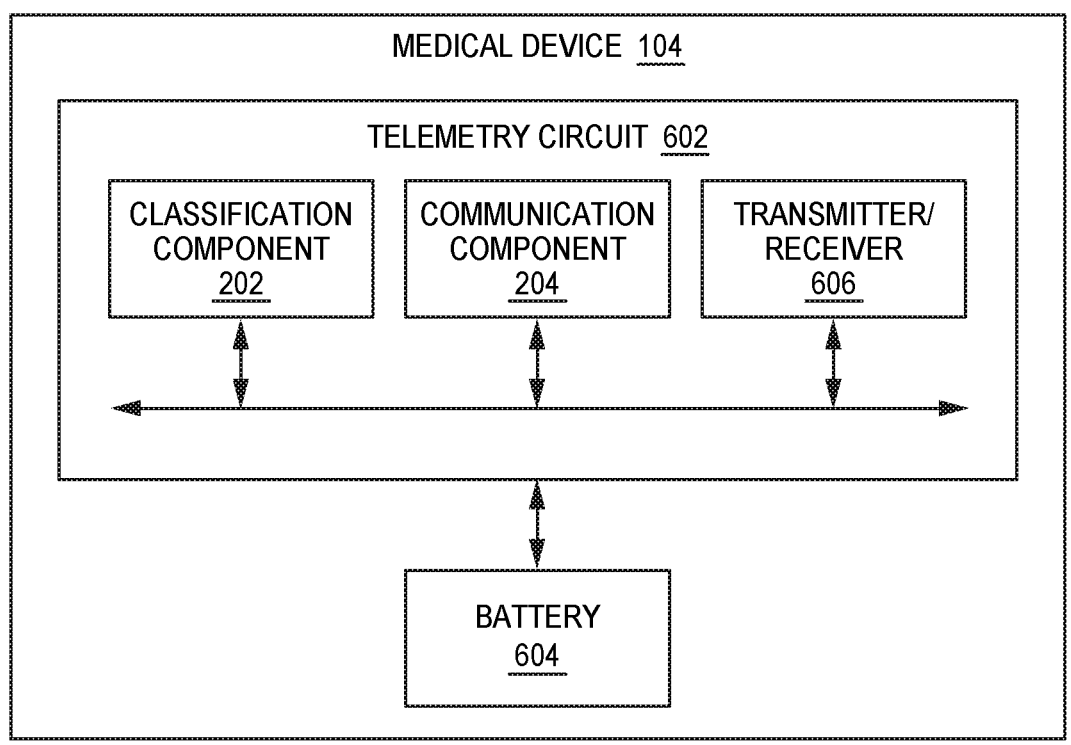
FIG. 6 illustrates an example, non-limiting medical device in accordance with one or more embodiments described herein.

FIG. 6 illustrates an example, non-limiting medical device 104 in accordance with one or more embodiments described herein. The medical device 104 includes a telemetry circuit 602 and a battery 604. Repetitive description of like elements employed in other embodiments described herein is omitted for sake of brevity.

The telemetry circuit 602 can be associated with the classification component 202 and/or the communication component 204. For instance, in an embodiment, the telemetry circuit 602 can include the classification component 202 and/or the communication component 204. Additionally, in certain embodiments, the telemetry circuit 602 can include a transmitter/receiver 606. In one example, the transmitter/receiver 606 can be a transceiver. The battery 604 can be, for example, a fixed battery within the medical device 104. The battery 604 can provide power to at least the telemetry circuit 602. However, it is to be appreciated that the battery 604 can be implemented as a different type of power source for the medical device 104. For instance, in an alternate embodiment, the battery 604 can be a capacitor, a charge pump, a mechanically derived power source (e.g., a MEMS device), or an induction component. Therefore, by providing a modulated beaconing rate for an advertising data packet as more fully disclosed herein, the classification component 202 and/or the communication component 204 can facilitate balancing current drain of the battery 604 to maximize utility and life of the battery 604 and/or the medical device 104. For example, the classification component 202 and/or the communication component 204 can be employed to calculate a beaconing rate for an advertising data packet that minimally impacts the battery 604 while also broadcasting the advertising data packet and/or delivering data associated with the medical device 104 to the external device 116. Longevity of the battery 604 and/or the medical device 104 can also be improved by employing a modulated beaconing rate for an advertising data packet via the classification component 202 and/or the communication component 204, as more fully disclosed herein. Moreover, telemetry latency associated with the telemetry circuit 602 can be mitigated and/or performance of the medical device 104 can be improved by employing a modulated beaconing rate for an advertising data packet via the classification component 202 and/or the communication component 204, as more fully disclosed herein.

In an embodiment, the communication component 204 can be configured to control operation of the transmitter/receiver 606 to facilitate establishment of a telemetry session between the medical device 104 and the external device 116 and control transmission. The communication component 204 can also be configured to control operation of the transmitter/receiver 606 to facilitate reception of data packets by the medical device 104. The type of the transmitter/receiver 606 can vary depending on the type of telemetry protocol the medical device 104 is configured to employ. In some embodiments, the transmitter/receiver 606 can be configured to perform different types of telemetry protocols. In other embodiments, the medical device 104 can include a plurality of different transmitters/receivers that are respectively configured to perform different types of telemetry communication protocols. In some embodiments, rather than including a transmitter and a receiver that do not share common circuitry, the medical device 104 can include a transceiver.

FIGS. 7, 8, 9 and 10 illustrate flow diagrams of example, non-limiting methods facilitating improved telemetry between a medical device and an external device in accordance with one or more embodiments described herein. While, for purposes of simplicity of explanation, the methodologies are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices.

Figure 7:
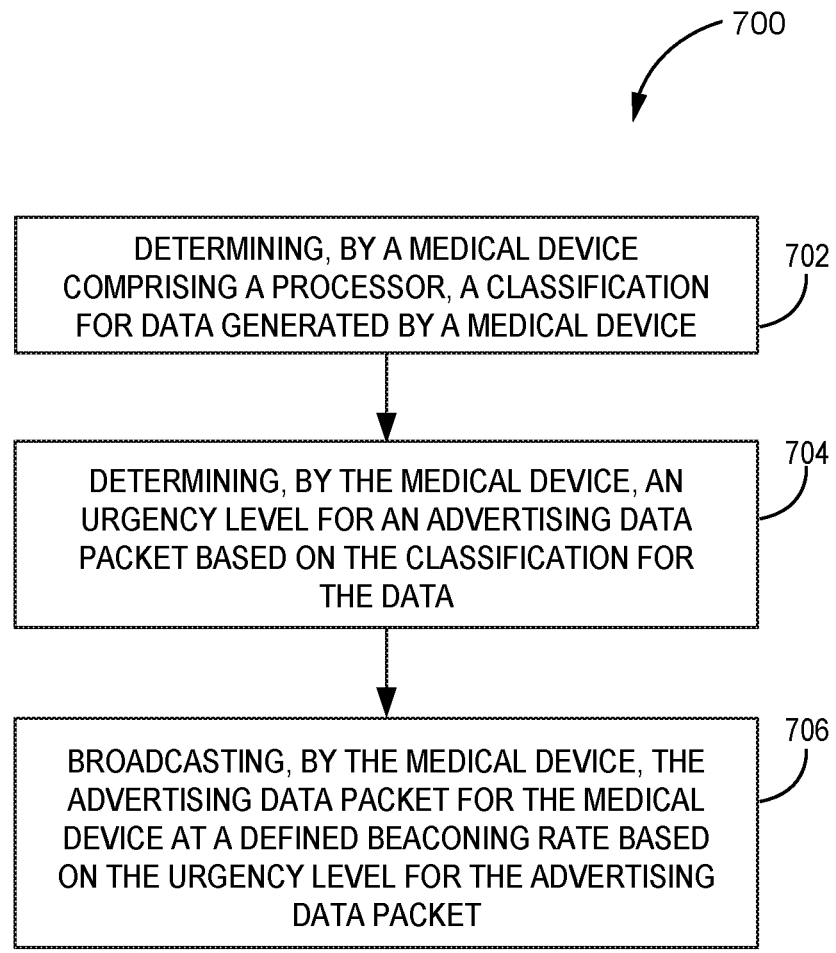
FIGS. 7, 8, 9 and 10 illustrate flow diagrams of example, non-limiting methods facilitating improved telemetry between a medical device and an external device in accordance with one or more embodiments described herein.

Referring now to FIG. 7, shown is a flow diagram of an example method 700 facilitating improved telemetry between a medical device and an external device in accordance with one embodiment. In some embodiments of method 700, a medical device (e.g., medical device 104) employs a classification component (e.g., classification component 202) and/or a communication component (e.g., communication component 204) to facilitate telemetry between the medical device and an external device. Repetitive description of like elements employed in other embodiments described herein is omitted for sake of brevity.

At 702, a classification for data generated by a medical device can be determined by a medical device comprising a processor (e.g., by the classification component 202). For example, the medical device can classify medical data generated by the medical device, remote monitoring data generated by the medical device, patient data generated by the medical device, and/or other data generated by the medical device. Medical data can include medical data read or otherwise obtained by the medical device, electrical signals sensed and/or generated by the medical device, a voltage or current provided by the medical device, a medical dosage provided by the medical device, etc. Remote monitoring data can include, for example, analysis data associated with the medical device and/or a patient, monitoring data for a condition associated with the medical device and/or the patient, etc. Patient data can include, for example, a name of a patient, a date of birth of a patient, a medical history associated with a patient, a medical identification or number associated with the patient, etc.

At 704, an urgency level for an advertising data packet can be determined by the medical device (e.g., by the classification component 202) based on the classification for the data. For example, the urgency level can correspond to a defined event associated with the data. The urgency level can be selected from a set of urgency levels. For instance, the set of urgency levels can include different urgency levels associated with different beaconing rates or different types of events related to the data.

At 706, the advertising data packet for the medical device can be broadcasted by the medical device (e.g., by the communication component 204) at a defined beaconing rate based on the urgency level for the advertising data packet. For example, a frequency of occurrence for repeatedly broadcasting the advertising data packet can be modulated based on the urgency level for the advertising data packet. In another example, telemetry polling of the advertising data packet can be dynamically modified based on the urgency level for the advertising data packet. Because configuration of an advertising data packet and communication between the medical device (e.g., the medical device 104) and the external device 116 is established from a combination of electrical and mechanical components and circuitry, and due to the inserting (e.g., encoding) of information associated with the implantable device (e.g., the medical device 104) within the advertising data packet as described herein, a human is unable to replicate or perform the subject data packet configuration and/or the subject communication between the implantable device and the external device. For example, a human is unable to encode information within an advertising data packet, transmit an advertising data packet (e.g., via an advertising communication channel), etc. Moreover, a human is unable to packetize a data packet that includes a sequence of bits corresponding to information associated with a medical device, a human cannot wirelessly broadcast an advertising data packet at a particular defined beaconing rate via a communication channel, etc.

Figure 8:
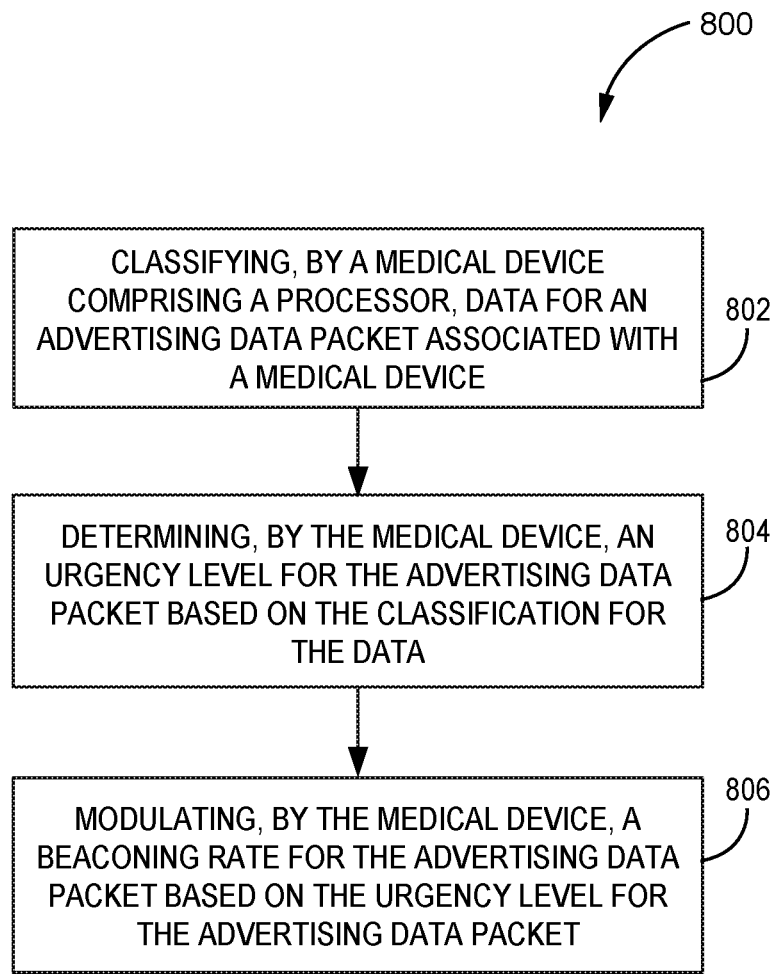

Turning now to FIG. 8, shown is a method 800 facilitating improved telemetry between a medical device and an external device in accordance with another embodiment. In some embodiments of method 800, a medical device (e.g., medical device 104) employs a classification component (e.g., classification component 202) and/or a communication component (e.g., communication component 204) to facilitate telemetry between the medical device and an external device. Repetitive description of like elements employed in other embodiments described herein is omitted for sake of brevity.

At 802, data for an advertising data packet associated with a medical device can be classified by a medical device comprising a processor (e.g., by the classification component 202). For example, medical data included in the advertising data packet, remote monitoring data included in the advertising data packet, patient data included in the advertising data packet, and/or other data included in the advertising data packet can be classified. Medical data can include medical data read or otherwise obtained by the medical device, electrical signals sensed and/or generated by the medical device, a voltage or current provided by the medical device, a medical dosage provided by the medical device, etc. Remote monitoring data can include, for example, analysis data associated with the medical device and/or a patient, monitoring data for a condition associated with the medical device and/or the patient, etc. Patient data can include, for example, a name of a patient, a date of birth of a patient, a medical history associated with a patient, a medical identification or number associated with the patient, etc.

At 804, an urgency level for the advertising data packet can be determined by the medical device (e.g., by the classification component 202) based on the classification for the data. For example, the urgency level can correspond to a defined event associated with the data. The urgency level can be selected from a set of urgency levels. For instance, the set of urgency levels can include different urgency levels associated with different beaconing rates or different types of events related to the data.

At 806, a beaconing rate for the advertising data packet can be modulated by the medical device (e.g., by the communication component 204) based on the urgency level for the advertising data packet. For example, a rate for broadcasting the advertising data packet can be modulated based on the urgency level for the advertising data packet.

In an embodiment, the beaconing rate can be increased or decreased based on a determination that the urgency level for the advertising data packet corresponds to a defined event associated with the data. In another embodiment, the beaconing rate can be decreased based on a determination that a communication connection is established between the medical device and an external device. Because classification and/or modulation of electronic information is performed from a combination of electrical and mechanical components and circuitry, a human is unable to replicate or perform these operations.

Figure 9:
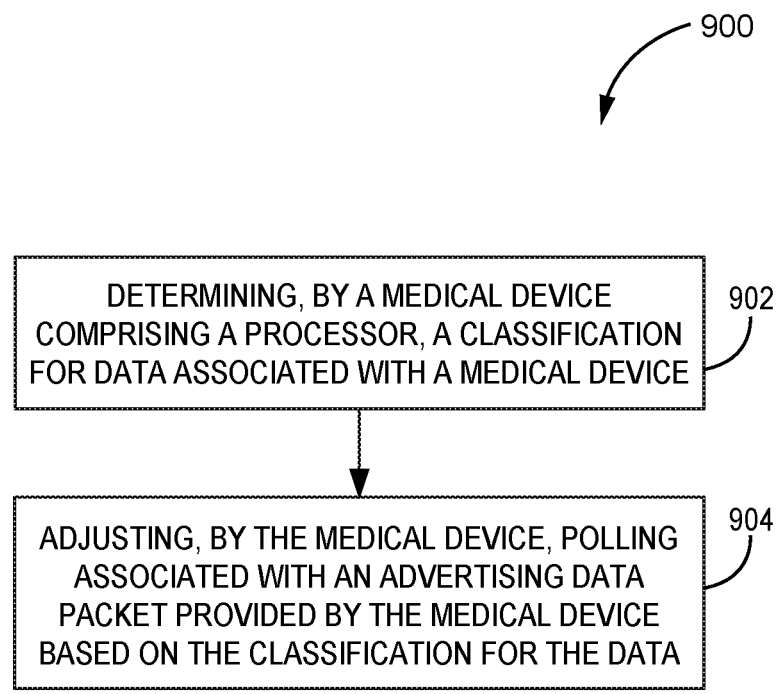

Turning now to FIG. 9, shown is a method 900 facilitating improved telemetry between a medical device and an external device in accordance with yet another embodiment. In some embodiments of method 900, a medical device (e.g., medical device 104) employs a classification component (e.g., classification component 202) and/or a communication component (e.g., communication component 204) to facilitate telemetry between the medical device and an external device. Repetitive description of like elements employed in other embodiments described herein is omitted for sake of brevity.

At 902, a classification for data associated with a medical device can be determined by a medical device comprising a processor (e.g., by the classification component 202). For example, medical data associated with the medical device, remote monitoring data associated with the medical device, patient data associated with the medical device, and/or other data associated with the medical device can correlated to a defined urgency level and/or a defined event. At 904, polling associated with an advertising data packet provided by the medical device can be adjusted by the medical device (e.g., by the communication component 204) based on the classification for the data. For example, a beaconing rate of the advertising data packet and/or an interval of time for broadcasting the advertising data packet can be modulated based on the classification for the data. Because classification and/or polling of signals over a wireless channel is performed from a combination of electrical and mechanical components and circuitry, a human is unable to replicate or perform these operations.

Figure 10:
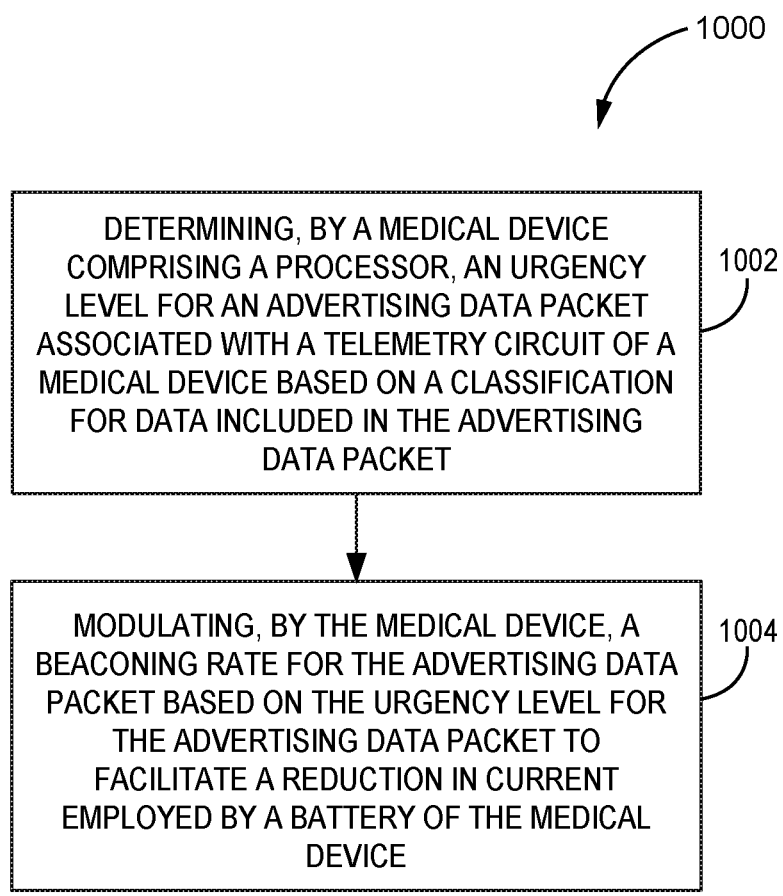

FIG. 10 shows a method 1000 facilitating improved telemetry between a medical device and an external device in accordance with yet another embodiment. In some embodiments of method 1000, a medical device (e.g., medical device 104) employs a classification component (e.g., classification component 202) and/or a communication component (e.g., communication component 204) to facilitate telemetry between the medical device and an external device. Repetitive description of like elements employed in other embodiments described herein is omitted for sake of brevity.

At 1002, an urgency level for an advertising data packet associated with a telemetry circuit of a medical device can be determined by a medical device comprising a processor (e.g., by the classification component 202) based on a classification for data included in the advertising data packet. For example, the urgency level can correspond to a defined event associated with the data. At 1004, a beaconing rate for the advertising data packet can be modulated by the medical device (e.g., by the communication component 204) based on the urgency level for the advertising data packet to facilitate a reduction in current employed by a battery of the medical device. For example, a lower urgency level for the advertising data packet can correspond to a lower beaconing rate for the advertising data packet to facilitate reduction in current employed by the battery and/or increased longevity of the battery. Because classification and/or transmission of signals over a wireless channel is performed from a combination of electrical and mechanical components and circuitry, a human is unable to replicate or perform these operations.

Figure 11:
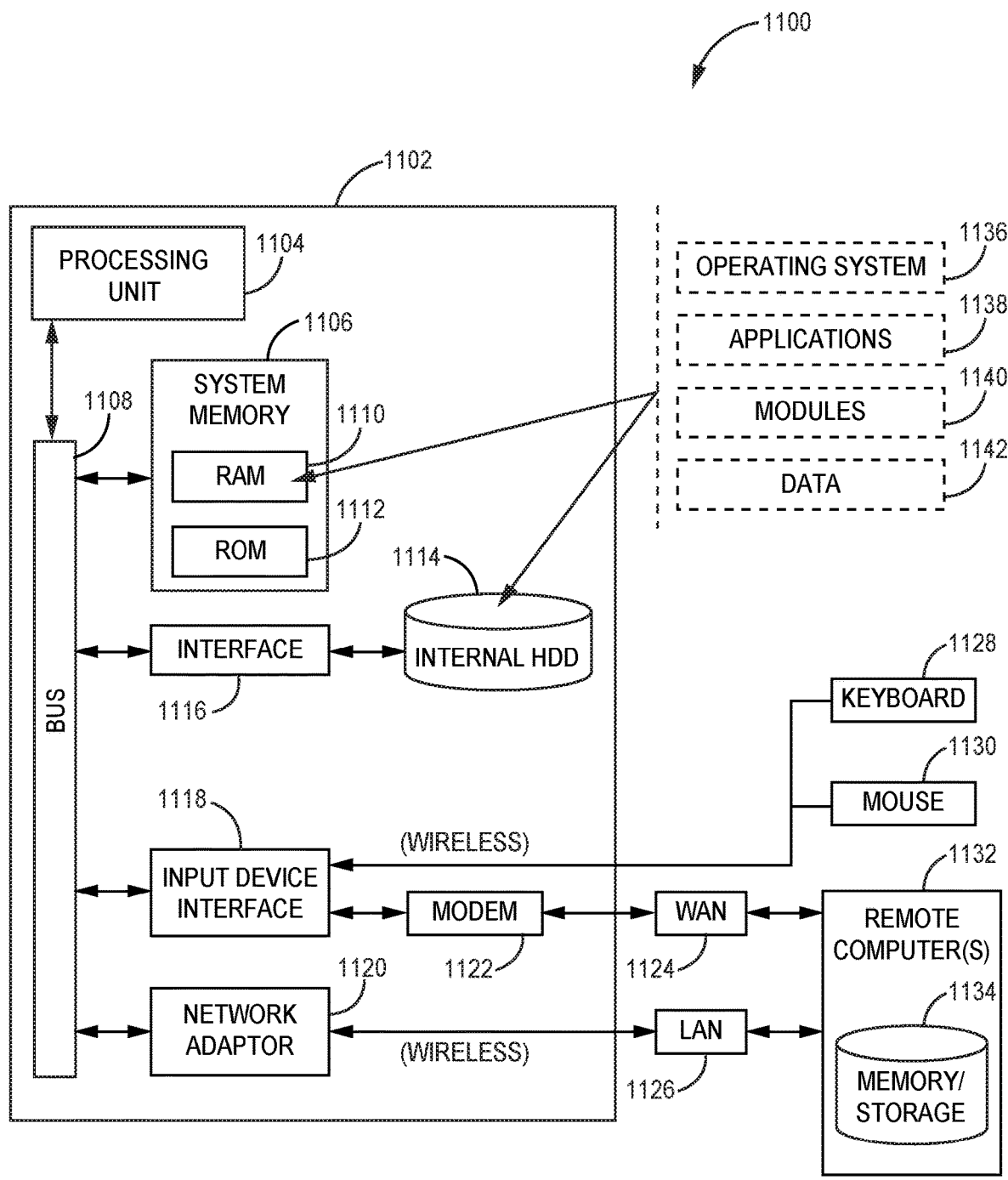
FIG. 11 illustrates a block diagram of an example, non-limiting computer operable to facilitate improved telemetry between a medical device and an external device in accordance with one or more embodiments described herein.

FIG. 11 illustrates a block diagram of a computer operable to facilitate improved telemetry between a medical device and an external device in accordance with one or more embodiments described herein. For example, in some embodiments, the computer can be or be included within medical device 104 and/or external device 116 (or any component of the medical device 104 and/or external device 116). Repetitive description of like elements employed in other embodiments described herein is omitted for sake of brevity.

In order to provide additional context for one or more embodiments described herein, FIG. 11 and the following discussion are intended to provide a brief, general description of a suitable computing environment 1100 in which the one or more embodiments described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory, computer-readable media or computer-readable storage media, is to be understood to exclude only propagating intangible signals per se as a modifier and does not relinquish coverage of all standard storage, memory, computer-readable media or computer-readable storage media that are not only propagating intangible signals per se.

In this regard, the term "non-transitory" herein as applied to storage, memory, computer-readable media or computer-readable storage media, is to be understood to exclude only propagating transitory signals per se as a modifier and does not relinquish coverage of all standard storage, memory, computer-readable media or computer-readable storage media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of the data signal's characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 11, example environment 1100 for implementing one or more embodiments of the embodiments described herein includes computer 1102, computer 1102 including processing unit 1104, system memory 1106 and system bus 1108. System bus 1108 couples system components including, but not limited to, system memory 1106 to processing unit 1104. Processing unit 1104 can be any of various commercially available processors. Dual microprocessors and other multi processor architectures can also be employed as processing unit 1104.

System bus 1108 can be any of several types of bus structure that can further interconnect to a memory bus (with or without a memory controller), a peripheral bus, and a local bus using any of a variety of commercially available bus architectures. System memory 1106 includes RAM 1110 and ROM 1112. A basic input/output system (BIOS) can be stored in a non-volatile memory such as ROM, erasable programmable read only memory (EPROM), EEPROM, which BIOS contains the basic routines that help to transfer information between elements within computer 1102, such as during startup. RAM 1110 can also include a high-speed RAM such as static RAM for caching data.

Computer 1102 further includes internal hard disk drive (HDD) 1114 (e.g., Enhanced Integrated Drive Electronics (EIDE), Serial Advanced Technology Attachment (SATA)). HDD 1114 can be connected to system bus 1108 by hard disk drive interface 1116. The drives and their associated computer-readable storage media provide nonvolatile storage of data, data structures, computer-executable instructions, and so forth. For computer 1102, the drives and storage media accommodate the storage of any data in a suitable digital format.

A number of program modules can be stored in the drives and RAM 1110, including operating system 1136, one or more application programs 1138, other program modules 1140 and program data 1142. All or portions of the operating system, applications, modules, and/or data can also be cached in RAM 1110. The systems and methods described herein can be implemented utilizing various commercially available operating systems or combinations of operating systems.

A mobile device can enter commands and information into computer 1102 through one or more wireless input devices, e.g., wireless keyboard 1128 and a pointing device, such as wireless mouse 1130. Other input devices (not shown) can include a smart phone, tablet, laptop, wand, wearable device or the like. These and other input devices are often connected to the processing unit 1104 through input device interface 1118 that can be coupled to system bus 1108, but can be connected by other interfaces, such as a parallel port, an IEEE serial port, a game port and/or a universal serial bus (USB) port.

Computer 1102 can operate in a networked environment using logical connections via wired and/or wireless communications to one or more remote computers, such as remote computer(s) 1132. Remote computer(s) 1132 can be a workstation, a server computer, a router, a personal computer, portable computer, microprocessor-based entertainment appliance, a peer device or other common network node, and typically includes many or all of the elements described relative to computer 1102, although, for purposes of brevity, only memory/storage device 1134 is illustrated. The logical connections depicted include wired/wireless connectivity to a local area network (LAN) 1126 and/or larger networks, e.g., WAN 1124, as well as smaller PANs involving a few devices (e.g., at least two). LAN and WAN networking environments are commonplace in the home, offices (e.g., medical facility offices, hospital offices) and companies, and facilitate enterprise-wide computer networks, such as intranets, all of which can connect to a global communications network (e.g., the Internet).

When used in a LAN networking environment, computer 1102 can be connected to local network through a wired and/or wireless communication network interface or adapter 1120. Adapter 1120 can facilitate wired or wireless communication to LAN 1126, which can also include a wireless access point (AP) connected to the LAN 1126 for communicating with adapter 1120.

When used in a WAN networking environment, computer 1102 can include modem 1122 or can be connected to a communications server on WAN 1124 or has other means for establishing communications over WAN 1124, such as by way of the Internet. Modem 1122, which can be internal or external and a wired or wireless device, can be connected to system bus 1108 via input device interface 1118. In a networked environment, program modules depicted relative to computer 1102 or portions thereof, can be stored in a remote memory/storage device. It will be appreciated that the network connections shown are example and other means of establishing a communications link between the computers can be used.

Computer 1102 can be operable to communicate with any wireless devices or entities operatively disposed in wireless communication via any number of protocols, including, but not limited to, NFC, Wi-Fi and/or BLUETOOTH® wireless protocols. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 centimeters of an implanted NFC component. NFC typically provides a maximum data rate of 424 kilobits per second (Kbps), although data rates can range from 6.67 Kbps to 828 Kbps. NFC typically operates at the frequency of 13.56 megahertz (MHz). NFC technology communication is typically over a range not exceeding 0.2 meters (m) and setup time can be less than 0.1 seconds. Low power (e.g., 15 milliamperes (mAs)) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments of devices described herein can employ artificial intelligence (AI) to facilitate automating one or more features described herein. The embodiments (e.g., in connection with automatically identifying acquired cell sites that provide a maximum value/benefit after addition to an existing communication network) can employ various AI-based schemes for carrying out one or more embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)$=confidence (class). Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments is intended to include, without being limited to, these and any other suitable types of memory.

As used herein, terms such as "data storage," "database," and substantially any other information storage component relevant to operation and functionality of a component, refer to "memory components," or entities embodied in a "memory" or components including the memory. It will be appreciated that the memory components or computer-readable storage media, described herein can be either volatile memory or nonvolatile memory or can include both volatile and nonvolatile memory.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

What has been described above includes mere examples of one or more embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A medical device configured to be employed by a patient, comprising:
   a housing;
   a memory, within the housing, that stores executable components; and
   circuitry, within the housing, and configured to at least one of obtain sensed physiological data associated with the patient or deliver a therapy to the patient;
   a processor, within the housing, that executes the executable components stored in the memory, wherein the executable components comprise:
      a classification component configured to determine a classification for data generated by the medical device and to determine an urgency level for an advertising data packet based on the classification for the data, wherein the advertising data packet is a data packet that facilitates establishment of a connection with another device; and
      a communication component configured to:
         broadcast the advertising data packet for the medical device at a defined beaconing rate based on the urgency level for the advertising data packet, wherein the advertising data packet for the medical device is broadcast at the defined beaconing rate a plurality of times over an advertising period;
         establish the connection with the other device; and
         transmit the data generated by the medical device via the established communication channel, wherein transmission of the data is via a set of packets distinct from the advertising data packet.

2. The medical device of claim 1, wherein the communication component is configured to broadcast the advertising data packet via modulation of the broadcast at the defined beaconing rate.

3. The medical device of claim 1, wherein the communication component is configured to increase the defined beaconing rate based on a determination that the urgency level for the advertising data packet corresponds to a defined event associated with the data.

4. The medical device of claim 1, wherein the communication component is further configured to decrease the defined beaconing rate based on a determination that the urgency level for the advertising data packet corresponds to a defined event associated with the data.

5. The medical device of claim 1, wherein the urgency level for the advertising data packet corresponds to a defined event.

6. The medical device of claim 1, wherein the urgency level for the advertising data packet corresponds to a defined medical event associated with the data or a processing event associated with the medical device.

7. The medical device of claim 1, wherein the urgency level for the advertising data packet corresponds to a defined medical event associated with a cardiac rhythm reading for the sensed physiological data.

8. The medical device of claim 1, wherein the communication component is configured to decrease the defined beaconing rate based on a determination that a communication connection is established between the medical device and an external device.

9. The medical device of claim 1, wherein the communication component is configured to modify the defined beaconing rate based on historical data indicative of a history of data exchanges with respect to an external device.

10. The medical device of claim 1, wherein the communication component is configured to modify the defined beaconing rate based on time data indicative of a timestamp associated with the broadcast of the advertising data packet.

11. The medical device of claim 1, wherein the defined beaconing rate is a first defined beaconing rate, and wherein the communication component is further configured to modify the defined beaconing rate to a second defined beaconing rate based on receipt of input by the medical device.

12. The medical device of claim 1, wherein the defined beaconing rate is a first defined beaconing rate, and wherein the communication component is further configured to modify the defined beaconing rate to a second defined beaconing rate based on longevity data indicative of a lifespan period for a battery of the medical device.

13. The medical device of claim 1, wherein the communication component is configured to broadcast the advertising data packet at the defined beaconing rate via a communication channel associated with a communication protocol utilizing a level of energy consumption that is less than a defined threshold.

14. The medical device of claim 1, wherein the medical device is an implantable medical device configured to be at least partially implanted within the patient.

15. A method, comprising:
   classifying, by a medical device comprising a processor, data for an advertising data packet associated with the medical device;
   determining, by the medical device, an urgency level for the advertising data packet based on the classifying for the data, wherein the advertising data packet is a data packet that facilitates establishment of a connection with another device;
   modulating, by the medical device, a beaconing rate for the advertising data packet based on the urgency level for the advertising data packet, wherein the advertising data packet for the medical device is broadcast at the modulated beaconing rate a plurality of times over an advertising period;
   establishing, by the device, a connection with the other device; and
   transmitting, by the device, the data generated by the medical device via the established communication channel.

16. The method of claim 15, wherein the modulating the beaconing rate for the advertising data packet comprises increasing the beaconing rate based on a determination that the urgency level for the advertising data packet corresponds to a defined event associated with the data.

17. The method of claim 15, wherein the modulating the beaconing rate for the advertising data packet comprises decreasing the beaconing rate based on a determination that the urgency level for the advertising data packet corresponds to a defined event associated with the data.

18. The method of claim 15, wherein the modulating the beaconing rate for the advertising data packet comprises decreasing the beaconing rate based on a determination that a communication connection is established between the medical device and an external device.

19. An apparatus, comprising:
   a memory that stores executable components; and
   a processor that executes the executable components stored in the memory, wherein the executable components comprise:
      a user feedback component configured to process user input data received via the apparatus; and a communication component configured to:
   transmit the user input data to a medical device via a first communication channel; and
   scan for an advertising data packet broadcast via a second communication channel, wherein the advertising data packet is a data packet that facilitates establishment of a connection, wherein the advertising data packet is broadcast at a defined beaconing rate based on an urgency level for the advertising data packet to establish the connection with the apparatus and to transmit the data generated by the medical device to the apparatus via the established communication channel, and wherein the advertising data packet for the medical device is broadcast at the defined beaconing rate a plurality of times over an advertising period.

20. The apparatus of claim 19, wherein the communication component is configured to communicate with the medical device via a third communication channel based on a determination that the advertising data packet satisfies a defined criterion.

21. The apparatus of claim 19, wherein the user feedback component is further configured to receive, via the apparatus, data that includes an interval of time for broadcasting the advertising data packet.

22. A non-transitory computer readable medium comprising computer executable instructions that, based on execution, cause a medical device including at least one processor to perform operations, comprising:
   determining a classification for data associated with the medical device;
   adjusting polling associated with an advertising data packet provided by the medical device based on the classification for the data, wherein the advertising data packet is a data packet that facilitates establishment of a connection with a device, and wherein the advertising data packet for the medical device is broadcast a plurality of times over an advertising period in accordance with the adjusted polling;
   establishing the connection with the device; and
   transmitting the data generated by the medical device via the established communication channel.

23. The non-transitory computer readable medium of claim 22, wherein the operations further comprise:
   determining an urgency level for the advertising data packet based on the classification for the data.

24. The non-transitory computer readable medium of claim 22, wherein the adjusting comprises increasing or decreasing a defined beaconing rate for the advertising data packet.

25. A system comprising:
   a medical device comprising:
      a classification component configured to determine a classification for data included in an advertising data packet associated with a telemetry communication protocol; and
      a communication component configured to:
         modulate the advertising data packet at a defined beaconing rate based on the classification for the data, wherein the advertising data packet is a data packet that facilitates establishment of a connection with another device, and wherein the advertising data packet for the medical device is broadcast at the defined beaconing rate a plurality of times over an advertising period;
         establish a connection with a second device; and
         transmit the data generated by the medical device via the established communication channel; and
   the second device configured to perform telemetry communication with the medical device using the telemetry communication protocol and the advertising data packet.

26. The system claim 25, wherein the classification component is further configured to determine an urgency level for the advertising data packet based on the classification for the data.

27. The system claim 26, wherein the communication component is further configured to modulate the advertising data packet at the defined beaconing rate based on the urgency level for the advertising data packet.

28. The system claim 25, wherein the communication component is configured to broadcast the advertising data packet at the defined beaconing rate based on the classification for the data.

* * * * *